(12) United States Patent
Nagata et al.

(10) Patent No.: US 10,803,845 B2
(45) Date of Patent: Oct. 13, 2020

(54) AUTOMATIC PERFORMANCE DEVICE AND AUTOMATIC PERFORMANCE METHOD

(71) Applicants: Roland Corporation, Shizuoka (JP); Meiji University, Tokyo (JP)

(72) Inventors: Akihiro Nagata, Shizuoka (JP); Tokio Takahashi, Shizuoka (JP); Shigeki Sagayama, Tokyo (JP); Kohei Hayashi, Tokyo (JP)

(73) Assignees: Roland Corporation, Shizouka (JP); Meiji University, Tokyo (JP)

( * ) Notice: Subject to any disclaimer, the term of this patent is extended or adjusted under 35 U.S.C. 154(b) by 0 days.

(21) Appl. No.: 16/412,439

(22) Filed: May 15, 2019

(65) Prior Publication Data
US 2019/0355338 A1 Nov. 21, 2019

(30) Foreign Application Priority Data
May 18, 2018 (JP) .................................. 2018-096439

(51) Int. Cl.
| | |
|---|---|
| *G10H 1/38* | (2006.01) |
| *A61B 5/0476* | (2006.01) |
| *G06K 9/00* | (2006.01) |
| *G10H 1/00* | (2006.01) |
| *G10H 1/34* | (2006.01) |

(52) U.S. Cl.
CPC ............. *G10H 1/38* (2013.01); *A61B 5/0476* (2013.01); *G06K 9/00302* (2013.01); *G10H 1/0008* (2013.01); *G10H 1/344* (2013.01); *A61B 2503/12* (2013.01); *G10H 2210/005* (2013.01)

(58) Field of Classification Search
CPC .... A61B 5/0476; A61B 2503/12; G10H 1/38; G10H 1/344; G10H 1/0008; G10H 2210/005; G06K 9/00302
USPC .......................................................... 84/610
See application file for complete search history.

(56) References Cited

U.S. PATENT DOCUMENTS

| | | | |
|---|---|---|---|
| 6,852,918 | B2 | 2/2005 | Kondo et al. |
| 7,358,433 | B2 | 4/2008 | Kondo et al. |
| 9,053,696 | B2 | 6/2015 | Watanabe et al. |
| 9,412,113 | B2 | 8/2016 | Watanabe et al. |
| 9,449,083 | B2 | 9/2016 | Watanabe et al. |

(Continued)

FOREIGN PATENT DOCUMENTS

| | | |
|---|---|---|
| EP | 1274069 | 1/2003 |
| EP | 2515249 | 10/2012 |

(Continued)

OTHER PUBLICATIONS

"Search Report of Europe Counterpart Application", dated Oct. 22, 2019, p. 1-p. 8.

*Primary Examiner* — Jeffrey Donels
(74) *Attorney, Agent, or Firm* — JCIPRNET

(57) ABSTRACT

The automatic performance device includes a storage part for storing a plurality of performance patterns, a performance part for playing a performance on the basis of a performance pattern stored in the storage part, an input part for inputting performance information through an input device that receives a performance operation of a user, and a selection part for selecting a performance pattern being a maximum likelihood estimation from the plurality of performance patterns stored in the storage part on the basis of the performance information input to the input part.

19 Claims, 15 Drawing Sheets

(56) References Cited

U.S. PATENT DOCUMENTS 9,563,701 B2 2/2017 Watanabe
2015/0013527 A1* 1/2015 Buskies .................. G10H 1/40
84/611

FOREIGN PATENT DOCUMENTS

| | | |
|---|---|---|
| JP | 2001337675 | 12/2001 |
| JP | 2003122355 | 4/2003 |
| JP | 2004287308 | 10/2004 |
| JP | 2004333611 | 11/2004 |
| JP | 2006098858 | 4/2006 |
| JP | 2007241181 | 9/2007 |
| JP | 2008096772 | 4/2008 |
| JP | 2008250020 | 10/2008 |
| JP | 2012048619 | 3/2012 |
| JP | 2012234167 | 11/2012 |
| WO | 2009032794 | 3/2009 |

* cited by examiner

| pattern name \ beat position | B1 | B2 | B3 | B4 | B5 | B6 | B7 | B8 | B9 | B10 | B11 | B12 | B13 | B14 | B15 | B16 | .. | B32 |
|---|---|---|---|---|---|---|---|---|---|---|---|---|---|---|---|---|---|---|
| P1 | J1 | | | | J2 | | | | J3 | | | | J4 | | | | | |
| P2 | J9 | | | | J10 | | J11 | | J12 | | | | J13 | | J14 | | | J8 |
| P3 | | | J20 | | J21 | | | | J24 | | J25 | | J26 | | | | .. | J20 |
| .. | | | | | | | | | | | | | | | | | .. | J36 |
| P10 | J71 | | J72 | | J73 | | J74 | | J75 | | J76 | | J77 | | J78 | | .. | J86 |
| .. | | | | | | | | | | | | | | | | | .. | .. |

input pattern table 11b

| state | pattern | beat position | pitch |
|---|---|---|---|
| J1 | P1 | B1 | do |
| J2 | P1 | B5 | mi |
| J3 | P1 | B9 | do |
| ... | ... | ... | ... |
| J11 | P2 | B7 | ◯ |
| ... | ... | ... | ... |
| J21 | P3 | B1 | do&mi |
| ... | ... | ... | ... |
| J74 | P10 | B7 | do |

FIG. 5(b)

output pattern table 11c

| pattern name | drum pattern | bass pattern | chord progression | arpeggio progression | effect | volume/velocity | timbre |
|---|---|---|---|---|---|---|---|
| P1 | DR1 | Ba1 | — | AR1 | Ef1 | Ve1 | Ti1 |
| P2 | DR2 | Ba2 | Ch1 | AR1 | Ef2 | Ve2 | Ti2 |
| P3 | DR1 | Ba5 | Ch2 | AR2 | Ef3 | Ve3 | Ti3 |
| ... | ... | ... | ... | ... | ... | ... | ... |
| P10 | DR7 | — | Ch5 | — | Ef10 | Ve10 | Ti20 |

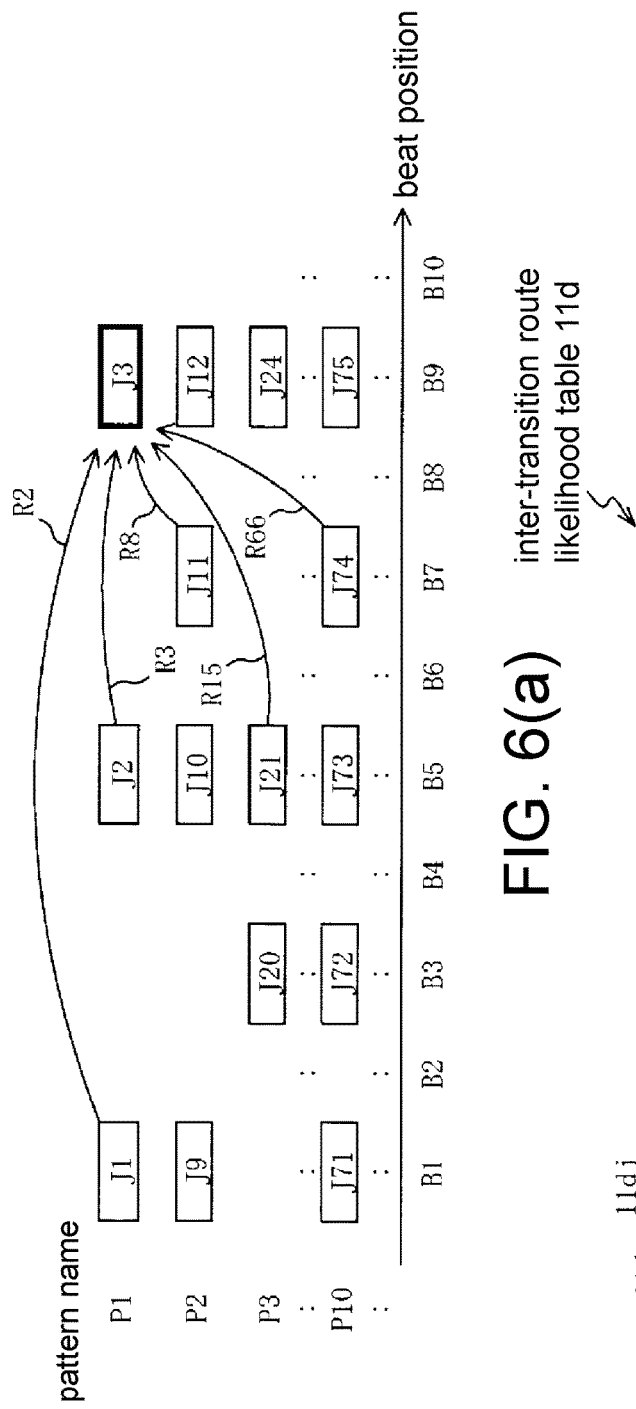

FIG. 7(a)

user evaluation likelihood table 11e

| pattern name | user evaluation likelihood |
|---|---|
| P1 | 0.1 |
| P2 | 0.1 |
| P3 | 0 |
| ... | ... |
| P10 | 0.3 |
| ... | ... |

pitch likelihood table 12f

| state | pitch likelihood |
|---|---|
| J1 | 1 |
| J2 | 0.4 |
| J3 | 1 |
| ... | ... |
| J11 | 1 |
| ... | ... |
| J21 | 0.54 |
| ... | ... |
| J74 | 1 |
| ... | ... |

FIG. 7(c)

accompaniment synchronization likelihood table 12g

| state | accompaniment synchronization likelihood |
|---|---|
| J1 | 0.4 |
| J2 | 0.7 |
| J3 | 0.2 |
| ... | ... |
| J11 | 0.4 |
| ... | ... |
| J21 | 0.5 |
| ... | ... |
| J74 | 0.3 |
| ... | ... |

| IOI likelihood table 12h | |
|---|---|
| route name | IOI likelihood |
| R1 | 0.3 |
| R2 | 0.4 |
| R3 | 0.6 |
| ... | ... |
| R8 | 0.3 |
| ... | ... |
| R15 | 0.6 |
| ... | ... |
| R66 | 1 |
| ... | ... |

FIG. 8(a)

| likelihood table 12i | |
|---|---|
| state | likelihood |
| J1 | 0.3 |
| J2 | 0.5 |
| J3 | 0.7 |
| ... | ... |
| J11 | 0.2 |
| ... | ... |
| J21 | 0.1 |
| ... | ... |
| J74 | 0.1 |
| ... | ... |

FIG. 8(b)

| previous likelihood table 12j | |
|---|---|
| state | previous likelihood |
| J1 | 0.4 |
| J2 | 0.7 |
| J3 | 0.3 |
| ... | ... |
| J11 | 0.2 |
| ... | ... |
| J21 | 0.1 |
| ... | ... |
| J74 | 0.1 |
| ... | ... |

FIG. 8(c)

AUTOMATIC PERFORMANCE DEVICE AND AUTOMATIC PERFORMANCE METHOD

CROSS-REFERENCE TO RELATED APPLICATION

This application claims the priority benefit of Japan Application No. 2018-096439, filed on May 18, 2018. The entirety of the above-mentioned patent application is hereby incorporated by reference herein and made a part of this specification.

BACKGROUND

Technical Field

The disclosure relates to an automatic performance device and an automatic performance method.

Description of Related Art

Patent Document 1 discloses an apparatus for searching for automatic accompaniment data. In this apparatus, when a user depresses a key on a keyboard of a rhythm input device 10, trigger data indicating that the key has been depressed, that is, a performance operation has been performed, and velocity data indicating the strength of depression of the key, that is, the strength of the performance operation, are input to an information processing device 20 as an input rhythm pattern which is in units of one bar.

The information processing device 20 has a database including a plurality of pieces of automatic accompaniment data. Each piece of automatic accompaniment data includes a plurality of parts, each having a unique rhythm pattern. When an input rhythm pattern has been input through the rhythm input device 10, the information processing device 20 searches for pieces of automatic accompaniment data having a rhythm pattern identical or similar to the input rhythm pattern and displays a list of the names or the like of the retrieved pieces of automatic accompaniment data. The information processing device 20 outputs a sound based on a piece of automatic accompaniment data selected by the user from the displayed list.

PATENT DOCUMENTS

[Patent Document 1] Japanese Patent Laid-Open No. 2012-234167
[Patent Document 2] Japanese Patent Laid-Open No. 2007-241181

As described above, in the apparatus of Patent Document 1, when selecting automatic accompaniment data, the user has to input an input rhythm pattern and then to select a desired piece of automatic accompaniment data from the displayed list, thus complicating the selection operation.

SUMMARY

An automatic performance device includes a storage part configured to store a plurality of performance patterns, a performance part configured to play a performance on the basis of one of the plurality of performance patterns stored in the storage part, an input part configured to input performance information through an input device configured to receive a performance operation of a user, and a selection part configured to select a performance pattern being a maximum likelihood estimation from the plurality of performance patterns stored in the storage part on the basis of the performance information input to the input part.

An automatic performance method causing a computer to execute automatic performance, the automatic performance method causing the computer to: store a plurality of performance patterns; play a performance on the basis of one of the stored plurality of performance patterns; input a performance operation of a user as a performance information; and select a performance pattern being a maximum likelihood estimation among the plurality of stored performance patterns on the basis of the input performance information and execute automatic performance with the selected performance pattern.

BRIEF DESCRIPTION OF THE DRAWINGS

FIG. 4 is a table for explaining states of input patterns.

FIG. 5($a$) is a diagram schematically showing an input pattern table and FIG. 5($b$) is a diagram schematically showing an output pattern table.

FIG. 6($a$) is a diagram for explaining a transition route and FIG. 6($b$) is a diagram schematically showing an inter-transition route likelihood table.

FIG. 7($a$) is a diagram schematically showing a user evaluation likelihood table, FIG. 7($b$) is a diagram schematically showing a pitch likelihood table, and FIG. 7($c$) is a diagram showing an accompaniment synchronization likelihood table.

FIG. 8($a$) is a diagram schematically showing an IOI likelihood table, FIG. 8($b$) is a diagram schematically showing a likelihood table, and FIG. 8($c$) is a diagram schematically showing a previous likelihood table.

DESCRIPTION OF THE EMBODIMENTS

The disclosure provides an automatic performance device and an automatic performance method which execute, in accordance with a user's free performance, an automatic performance suitable for the performance.

Here, examples of the "input device" include not only a keyboard mounted on a main body of the automatic performance device but also a keyboard of an external device that is configured separately from the automatic performance device.

The expression "all or some of musical sounds included in the plurality of performance patterns" means all or some of musical sounds included in each of all or some of the plurality of performance patterns.

According to an embodiment, the selection part of the automatic performance device is configured to execute a selection process of the performance pattern when performance information based on a performance operation of the user is input to the input part. It is to be noted that the "selection process of the performance pattern" is not necessarily performed every time performance information based on a performance operation of the user is input and may also be performed when a plurality of inputs of performance information have been made. Also, when a group of performance information has been input within a predetermined period of time, the "selection process of the performance pattern" may be performed in accordance with the input of the group of performance information within the predetermined period of time.

Here, examples of the "input device" include a keyboard or the like that is connected by wire or wirelessly to a computer on which the automatic performance method is executed.

Figure 1:
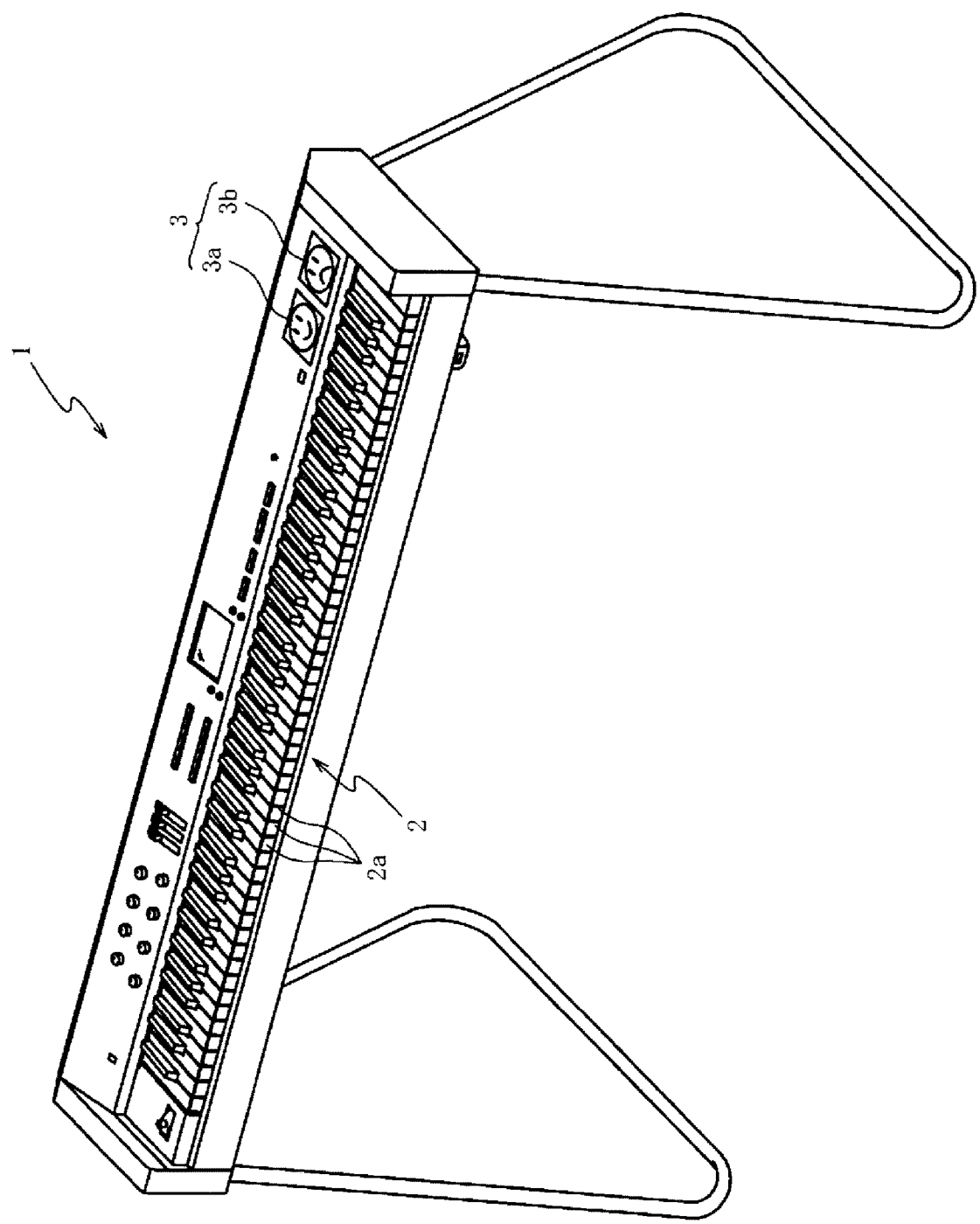
FIG. 1 is an external view of a synthesizer that is an embodiment.

Hereinafter, the embodiments will be described with reference to the accompanying drawings. FIG. 1 is an external view of a synthesizer 1 that is an embodiment. The synthesizer 1 is an electronic musical instrument (automatic musical instrument) that mixes and outputs (emits) a musical sound generated by a performance operation of a performer (user), a predetermined accompaniment sound, and the like. The synthesizer 1 can play an effect such as a reverberation, a chorus, or a delay by performing arithmetic processing on waveform data obtained by mixing a musical sound generated by the performer's performance, an accompaniment sound, and the like.

As shown in FIG. 1, the synthesizer 1 mainly includes a keyboard 2 and user evaluation buttons 3. A plurality of keys 2a are arranged on the keyboard 2, which is an input device for acquiring performance information generated by the performer's performance. Performance information according to the musical instrument digital interface (MIDI) standard corresponding to a key depression/release operation of a key 2a performed by the performer is output to a CPU 10 (see FIG. 2).

The user evaluation buttons 3 are buttons for outputting an evaluation (a high evaluation or a low evaluation) of the performer on the accompaniment sound and effect output from the synthesizer 1 to the CPU 10. The user evaluation buttons 3 include a high evaluation button 3a for outputting information indicating a high evaluation of the performer to the CPU 10 and a low evaluation button 3b for outputting information indicating a low evaluation of the performer to the CPU 10. The performer presses the high evaluation button 3a when the impression of the accompaniment sound and effect output from the synthesizer 1 is good and presses the low evaluation button 3b when the impression of the accompaniment sound and effect is not very good or poor. Information indicating a high or low evaluation corresponding to the pressed high or low evaluation button 3a or 3b is output to the CPU 10.

As will be described in detail later, the synthesizer 1 of the present embodiment estimates an output pattern on the basis of performance information of a key 2a generated by the performer from a plurality of output patterns, each of which is a combination of an accompaniment sound and an effect, and outputs the corresponding accompaniment sound and effect. Thereby, in accordance with a free performance of the performer, it is possible to output accompaniment sounds and effects suitable for the performance. Here, an output pattern of an accompaniment sound and an effect for which the performer has pressed the high evaluation button 3a many times is selected with higher priority. Thereby, in accordance with a free performance of the performer, it is possible to output accompaniment sounds and effects suitable for the performance.

Figure 2:
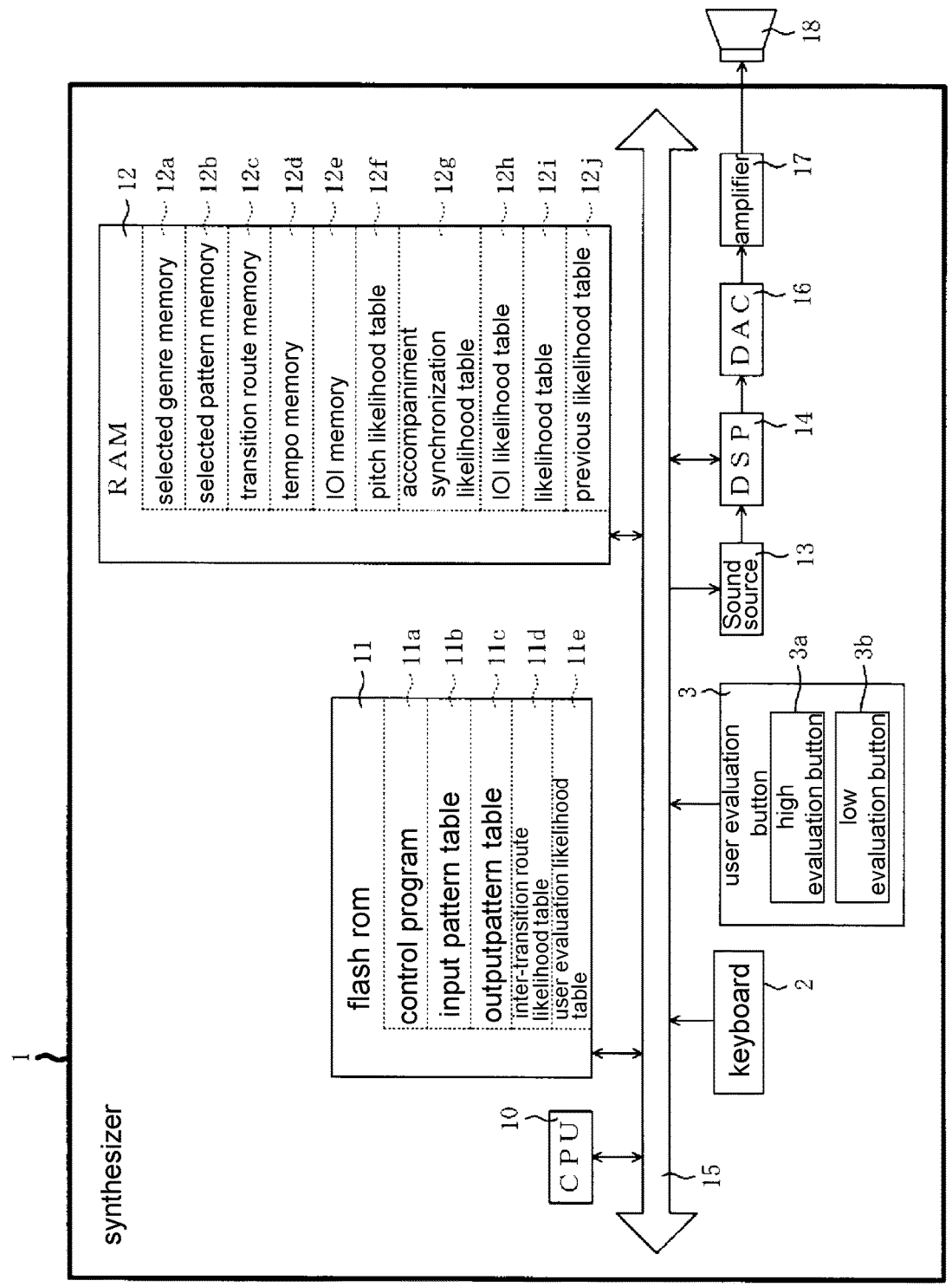
FIG. 2 is a block diagram showing an electrical configuration of a synthesizer.

Next, an electrical configuration of the synthesizer 1 will be described with reference to FIGS. 2 to 8. FIG. 2 is a block diagram showing the electrical configuration of the synthesizer 1. The synthesizer 1 has a CPU 10, a flash ROM 11, a RAM 12, the keyboard 2, the user evaluation buttons 3, a sound source 13, and a digital signal processor 14 (hereinafter referred to as a "DSP 14"), which are connected via a bus line 15. A digital-to-analog converter (DAC) 16 is connected to the DSP 14, an amplifier 17 is connected to the DAC 16, and a speaker 18 is connected to the amplifier 17.

Figure 9:
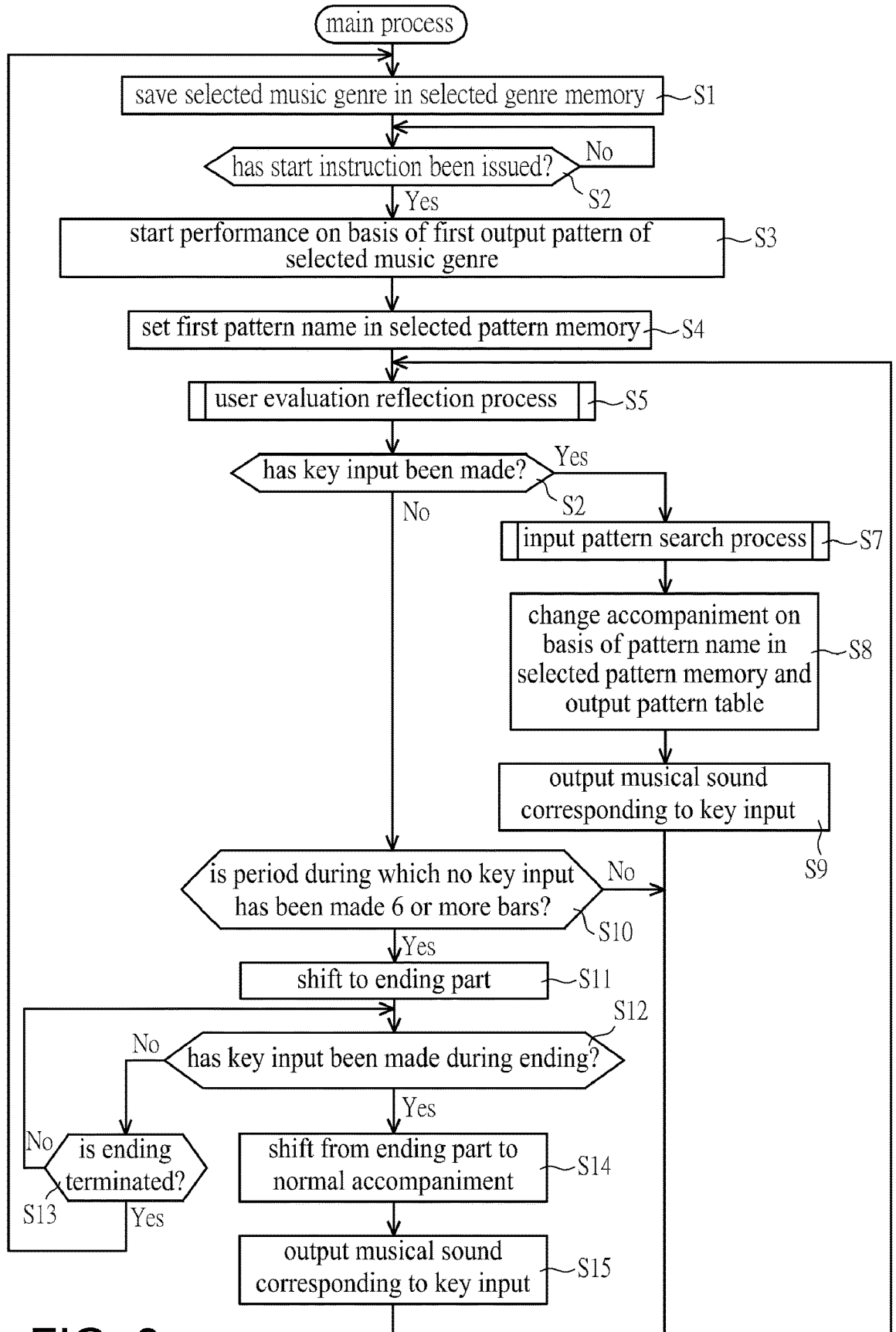
FIG. 9 is a flowchart of a main process.

The CPU 10 is an arithmetic device that controls each unit connected via the bus line 15. The flash ROM 11 is a rewritable nonvolatile memory in which a control program 11a, an input pattern table 11b, an output pattern table 11c, an inter-transition route likelihood table 11d, a user evaluation likelihood table 11e are provided. A main process of FIG. 9 is performed by the CPU 10 executing the control program 11a.

The input pattern table 11b is a data table that stores performance information and an input pattern that matches the performance information. Here, a beat position of an accompaniment sound, a state, and a pattern name in the synthesizer 1 of the present embodiment will be described with reference to FIG. 3.

Figures 3A, 3B:
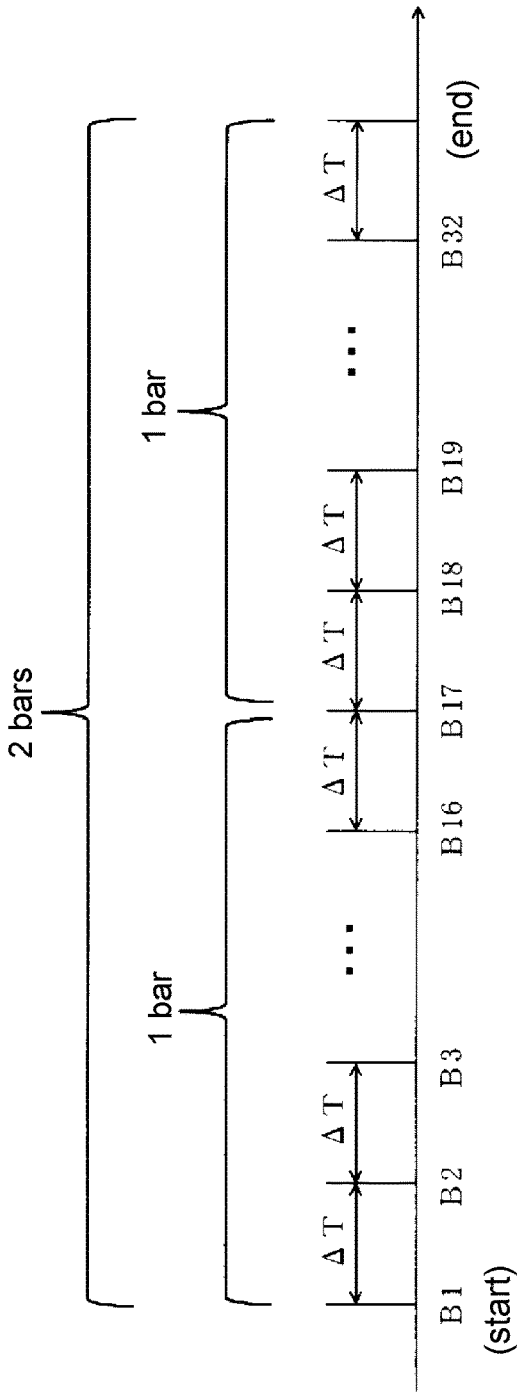
FIG. 3($a$) is a schematic diagram for explaining the beat position of an accompaniment sound and FIG. 3($b$) is a table showing examples of input patterns.

FIG. 3(a) is a schematic diagram for explaining the beat position of the accompaniment sound. In the synthesizer 1 of the present embodiment, a plurality of output patterns, each of which is a combination of an accompaniment sound and an effect, are stored, and an input pattern including a series of beat positions and pitches corresponding to each output pattern is set. On the basis of performance information of a key 2a generated by the performer and a beat position and a pitch of each input pattern, an input pattern "likely" for the performance information of the key 2a generated by the performer is estimated and an accompaniment sound and an effect of an output pattern corresponding to the estimated input pattern are output. Hereinafter, a combination of an input pattern and an output pattern will be referred to as a "pattern."

In the present embodiment, as shown in FIG. 3(a), the playing duration of the accompaniment sound of each output pattern has a length of two bars in common time. Beat positions B1 to B32 obtained by dividing the length of two bars equally by the length of a sixteenth note (that is, by dividing it into 32 equal parts) are each regarded as one temporal position unit. Here, time $\Delta T$ in FIG. 3(a) represents the length of a sixteenth note. An array of pitches corresponding to the accompaniment sounds and effects of an output pattern for the beat positions B1 to B32 constitutes an input pattern. Examples of such input patterns are shown in FIG. 3(b).

FIG. 3(b) is a table showing examples of input patterns. As shown in FIG. 3(b), pitches (do, re, mi, . . . ) for the beat positions B1 to B32 are set in each input pattern. Here, patterns P1, P2, . . . are each an identification name for associating an input pattern with an output pattern which will be described later.

For any beat position B1 to B32 in an input pattern, not only can a single pitch be set, but a combination of two or more pitches can also be designated. In the present embodiment, to designate that two or more pitches are input at the same time, the corresponding pitch names are linked by "&" at the beat position B1 to B32. For example, at the beat position B5 of the input pattern P3 in FIG. 3(b), pitches "do & mi" are designated, which designates that "do" and "mi" are input at the same time.

Further, for each beat position B1 to B32, it is also possible to designate that any pitch (a so-called wildcard pitch) is input. In the present embodiment, to designate that a wildcard pitch is input, "○" is designated for the beat position B1 to B32. For example, since the input of a wildcard pitch is designated at the beat position B7 of the input pattern P2 in FIG. 3(b), "○" is designated for the beat position B7.

In the input pattern, pitches are defined for beat positions B1 to B32 for which the input of performance information is designated, while no pitches are defined for beat positions B1 to B32 for which the input of performance information is not designated.

In the present embodiment, to manage combinations of beat positions B1 to B32 and pitches for the input pattern, each combination is defined as one "state." States of input patterns will be described below with reference to FIG. 4.

FIG. 4 is a table for explaining the states of input patterns. As shown in FIG. 4, states J1, J2, . . . are defined for beat positions B1 to B32 for which pitches are designated in order from the beat position B1 in the input pattern P1. Specifically, the beat position B1 of the input pattern P1 is defined as a state J1, the beat position B5 of the input pattern P1 is defined as a state J2, . . . , the beat position B32 of the input pattern P1 is defined as a state J8, and the beat position B1 of the input pattern P2 is defined as a state J9, subsequent to the state J8. Hereinafter, states J1, J2, . . . will each be abbreviated as a "state Jn" unless particularly distinguished.

In the input pattern table 11b in FIG. 2, the pattern name of a corresponding input pattern, a beat position B1 to B32, and a pitch are stored for each state Jn. The input pattern table 11b will be described below with reference to FIG. 5(a).

FIG. 5(a) is a diagram schematically showing the input pattern table 11b. The input pattern table 11b is a data table in which the pattern name of a corresponding input pattern, a beat position B1 to B32, and a pitch are stored for each state Jn for each music genre (such as rock, pop, and jazz) that can be designated in the synthesizer 1. In the present embodiment, the input pattern table 11b stores input patterns for each music genre and an input pattern corresponding to a selected music genre is referred to from the input pattern table 11b.

Specifically, input patterns corresponding to the music genre "rock" are stored in an input pattern table 11br, input patterns corresponding to the music genre "pop" are stored in an input pattern table 11bp, input patterns corresponding to the music genre "jazz" are stored in an input pattern table 11bj, and input patterns are similarly stored for other music genres. Hereinafter, the input pattern tables 11bp, 11br, 11bj, . . . in the input pattern table 11b will each be referred to as an "input pattern table 11bx" unless particularly distinguished.

When performance information of a key 2a is input, a "likely" state Jn is estimated from a beat position and a pitch of the performance information and a beat position and a pitch of an input pattern table 11bx corresponding to the selected music genre, an input pattern is acquired from the state Jn, and an accompaniment sound and an effect of an output pattern corresponding to the pattern name of the input pattern are output.

Referring back to FIG. 2, the output pattern table 11c is a data table that stores output patterns which are combinations of accompaniment sounds and effects for the patterns. The output pattern table 11c will be described below with reference to FIG. 5(b).

FIG. 5(b) is a diagram schematically showing the output pattern table 11c. Similar to the input pattern table 11b, the output pattern table 11c stores output patterns for each music genre. Specifically, in the output pattern table 11c, output patterns corresponding to the music genre "rock" are stored in an output pattern table 11cr, output patterns corresponding to the music genre "pop" are stored in an output pattern table 11cp, output patterns corresponding to the music genre "jazz" are stored in an output pattern table 11cj, and output patterns are similarly stored for other music genres. Hereinafter, the output pattern tables 11cp, 11cr, 11cj, . . . in the output pattern table 11c will each be referred to as an "output pattern table 11cx" unless particularly distinguished.

In an output pattern table 11cx, a drum pattern in which the rhythm pattern of a drum as an accompaniment sound is stored, a bass pattern in which the rhythm pattern of a bass is stored, a chord progression in which the progression of chords (harmonies) is stored, an arpeggio progression in which the progression of arpeggios is stored, an effect in which the mode of an effect is stored, a volume/velocity in which the volume/velocity value of a musical sound based on performance information of a key 2a generated by the performer or an accompaniment sound is stored, and a timbre in which the timbre of a musical sound based on performance information of a key 2a generated by the performer is stored are set for each output pattern.

Drum patterns DR1, DR2, . . . which are performance information of different drum performances are preset as the drum pattern and a drum pattern DR1, DR2, . . . is set for each output pattern. Bass patterns Ba1, Ba2, . . . which are performance information of different bass performances are preset as the bass pattern and a bass pattern Ba1, Ba2, . . . is set for each output pattern.

Chord progressions Ch1, Ch2, . . . which are performance information of different chord progressions are preset as the chord progression and a chord progression Ch1, Ch2, . . . is set for each output pattern. Arpeggio progressions AR1, AR2, . . . which are performance information of different arpeggio progressions are preset as the arpeggio progression and an arpeggio progression AR1, AR2, . . . is set for each output pattern.

The playing duration of each of the drum pattern DR1, DR2, . . . , the bass pattern Ba1, Ba2, . . . , the chord progression Ch1, Ch2, . . . , and the arpeggio progression AR1, AR2 . . . stored in the output pattern table 11cx as an accompaniment sound has a length of two bars as described above. Since the length of two bars is also a general unit in music expression, even if the same pattern is continued and the accompaniment sound is repeatedly output, it can be regarded as an accompaniment sound without causing discomfort to the performer or the audience.

Effects Ef1, Ef2, . . . of different modes are preset as the effect and an effect Ef1, Ef2, . . . is set for each output pattern. Volumes/velocities Ve1, Ve2, . . . of different values are preset as the volume/velocity and a volume/velocity Ve1, Ve2, . . . is set for each output pattern. Timbres Ti1, Ti2, . . . of different musical instruments or the like are preset as the timbre and a timbre Ti1, Ti2, . . . is set for each output pattern.

Further, the musical sound based on the performance information of the key 2a is output on the basis of the timbre Ti1, Ti2, . . . set in the selected output pattern, and an effect Ef1, Ef2, . . . and a volume/velocity Ve1, Ve2, . . . set in the selected output pattern are applied to the musical sound based on the performance information of the key 2a and the accompaniment sound.

Referring back to FIG. 2, the inter-transition route likelihood table 11d is a data table that stores a transition route Rm between states Jn, a beat distance which is the distance between beat positions B1 to B32 of the transition route Rm, and a pattern transition likelihood and a miskeying likelihood for the transition route Rm. Here, the transition route Rm and the inter-transition route likelihood table 11d will be described below with reference to FIG. 6.

FIG. 6(a) is a diagram for explaining the transition route Rm and FIG. 6(b) is a diagram schematically showing the inter-transition route likelihood table 11d. In FIG. 6(a), the horizontal axis indicates the beat positions B1 to B32. As time elapses, the beat position progresses from the beat position B1 to the beat position B32 and the state Jn in each pattern also changes as shown in FIG. 6(a). In the present embodiment, routes between states Jn assumed for transitions between the states Jn are preset. Hereinafter, the preset routes for transitions between the states Jn will be referred to as "transition routes R1, R2, R3, . . . ," and these will each be referred to as a "transition route Rm" unless particularly distinguished.

Transition routes to the state J3 are shown in FIG. 6(a). Roughly two types of transition routes are set as the transition routes to the state J3, the first for transitions from states Jn of the same pattern as the state J3 (that is, the pattern P1), the second for transitions from states Jn of a pattern different from the state J3.

A transition route R3 that transitions from a state J2 which is immediately prior to the state J3, and a transition route R2 which is a transition route from the state J1 which is two states prior to the state J3 are set as the transitions from states Jn of the same pattern P1 as the state J3. That is, in the present embodiment, no more than two transition routes, the first being a transition route that transitions from an immediately preceding state Jn, the second being a transition route of "sound skipping" that transitions from a state which was two states ago, are set as transitions to states Jn in the same pattern.

On the other hand, a transition route R8 that transitions from a state J11 of the pattern P2 to the state J3, a transition route R15 that transitions from a state J21 of the pattern P3 to the state J3, a transition route R66 that transitions from a state J74 of the pattern P10 to the state J3, and the like may be set as the transition routes that transition from states Jn of different patterns from the state J3. That is, transition routes where a transition source state Jn of a different pattern is immediately prior to the beat position of a transition destination state Jn are set as transition routes to states Jn in different patterns.

A plurality of transition routes Rm to the state J3 are set in addition to the transition routes illustrated in FIG. 6(a). One or a plurality of transition routes Rm to each state Jn are set similarly for the state J3.

A "likely" state Jn is estimated on the basis of the performance information of the key 2a and an accompaniment sound or an effect of an output pattern corresponding to an input pattern corresponding to the state Jn is output. In the present embodiment, a state Jn is estimated on the basis of the likelihood that is a numerical value set for each state Jn representing the "likelihood" between performance information of the key 2a and the state Jn. In the present embodiment, the likelihood for the state Jn is calculated by combining the likelihood based on the state Jn itself, the likelihood based on the transition route Rm, or the likelihood based on the pattern.

The pattern transition likelihood and the miskeying likelihood stored in the inter-transition route likelihood table 11dx are likelihoods based on the transition route Rm. Specifically, first, the pattern transition likelihood is a likelihood representing whether or not a transition source state Jn and a transition destination state Jn for the transition route Rm are in the same pattern. In the present embodiment, "1" is set to the pattern transition likelihood when the transition source and destination states Jn for the transition route Rm are in the same pattern and "0.5" is set to the pattern transition likelihood when the transition source and destination states Jn for the transition route Rm are in different patterns.

For example, in FIG. 6(b), "1" is set to the pattern transition likelihood of the transition route R3 since the transition source of the transition route R3 is the state J2 of the pattern P1 and the transition destination is the state J3 of the same pattern P1. On the other hand, the transition route R8 is a transition route between different patterns since the transition source of the transition route R8 is the state J11 of the pattern P2 and the transition destination is the state J3 of the pattern P1. Therefore, "0.5" is set to the pattern transition likelihood of the transition route R8.

Values are set for the pattern transition likelihood such that a value set for the pattern transition likelihood of a transition route Rm for the same pattern is greater than that for the pattern transition likelihood of a transition route Rm for different patterns. This is because the probability of staying in the same pattern is higher than the probability of transitioning to a different pattern in actual performances. Therefore, by estimating a transition destination state Jn of a transition route Rm to the same pattern with priority over a transition destination state Jn of a transition route Rm to a different pattern, it is possible to prevent transitions to different patterns and to prevent frequent changes in the output pattern. As a result, it is possible to prevent frequent changes in the accompaniment sound or the effect, and therefore it is possible to provide accompaniment sounds and effects with less discomfort to performers and audiences.

The miskeying likelihood stored in the inter-transition route likelihood table 11dx represents whether or not the transition source and destination states Jn of the transition route Rm are in the same pattern and further the transition source state Jn is two states prior to the transition destination state Jn, that is, whether or not the transition route Rm having the transition source and destination states Jn is due to sound skipping. In the present embodiment, "0.45" is set to the miskeying likelihood of transition routes Rm having transition source and destination states Jn due to sound skipping and "1" is set to the miskeying likelihood of transition routes Rm other than those due to sound skipping.

For example, in FIG. 6(b), "1" is set to the miskeying likelihood of the transition route R1 since the transition route R1 is a transition route between adjacent states J1 and J2 in the same pattern P1 and is not a transition route due to sound skipping. On the other hand, "0.45" is set to the miskeying likelihood of the transition route R2 since the transition destination state J3 of the transition route R2 is two states prior to the transition source state J1.

Transition routes Rm due to sound skipping in each of which a transition source state Jn is two states prior to a transition destination state Jn in the same pattern are also set as described above. In actual performances, the probability of the occurrence of a transition due to sound skipping is lower than the probability of the occurrence of a normal transition. Therefore, by setting a smaller value to the miskeying likelihood of a transition route Rm due to sound skipping than to the miskeying likelihood of a normal transition route Rm which is not due to sound skipping, as in actual performances, it is possible to estimate a transition destination state Jn of a normal transition route Rm with priority over a transition destination state Jn of a transition route Rm due to sound skipping.

Further, as shown in FIG. 6(b), in the inter-transition route likelihood table 11d, the transition source state Jn, the transition destination state Jn, the pattern transition likelihood, and the miskeying likelihood of the transition route Rm are stored for each transition route Rm in association with each other for each music genre designated in the synthesizer 1. In the present embodiment, the inter-transition route likelihood table 11d also includes an inter-transition route likelihood table stored for each music genre. An inter-transition route likelihood table corresponding to the music genre "rock" is defined as an inter-transition route likelihood table 11dr, an inter-transition route likelihood table corresponding to the music genre "pop" is defined as an inter-transition route likelihood table 11dp, an inter-transition route likelihood table corresponding to the music genre "jazz" is defined as an inter-transition route likelihood table 11dj, and inter-transition route likelihood tables are also defined for other music genres. Hereinafter, the inter-transition route likelihood tables 11dp, 11dr, 11dj, . . . in the inter-transition route likelihood table 11d will each be referred to as an "inter-transition route likelihood table 11dx" unless particularly distinguished.

Referring back to FIG. 2, the user evaluation likelihood table 11e is a data table that stores results of evaluation for output patterns during performance by the performer.

The user evaluation likelihood is a likelihood that is set for each pattern on the basis of an input through the user evaluation buttons 3 described above with reference to FIG. 1. Specifically, if the performer presses the high evaluation button 3a among the user evaluation buttons 3 (FIG. 1) for an accompaniment sound or effect being output, "0.1" is added to a user evaluation likelihood of a pattern corresponding to the accompaniment sound or effect being output. On the other hand, if the performer presses the low evaluation button 3b among the user evaluation buttons 3 (FIG. 1) for an accompaniment sound or effect being output, "0.1" is subtracted from a user evaluation likelihood of a pattern corresponding to the accompaniment sound or effect being output.

That is, a greater user evaluation likelihood is set for a pattern of an accompaniment sound or effect highly evaluated by the performer and a smaller user evaluation likelihood is set for a pattern of an accompaniment sound or effect lowly evaluated by the performer. Then, the user evaluation likelihood is applied to the likelihood of a state Jn corresponding to the pattern and a state Jn for the performance information of the key 2a is estimated on the basis of the user evaluation likelihood for each state Jn. Accordingly, an accompaniment sound and an effect of a pattern higher evaluated by the performer is output with priority, and therefore the accompaniment sound and effect based on the performer's preferences on performance can be output with higher probability. The user evaluation likelihood table 11e in which the user evaluation likelihood is stored will be described below with reference to FIG. 7(a).

FIG. 7(a) is a diagram schematically showing the user evaluation likelihood table 11e. The user evaluation likelihood table 11e is a data table in which the user evaluation likelihood based on the performer's evaluation is stored for each pattern for each music genre (such as rock, pop, and jazz). In the present embodiment, in the user evaluation likelihood table 11e, a user evaluation likelihood table corresponding to the music genre "rock" is defined as a user evaluation likelihood table 11er, a user evaluation likelihood table corresponding to the music genre "pop" is defined as a user evaluation likelihood table 11ep, a user evaluation likelihood table corresponding to the music genre "jazz" is defined as a user evaluation likelihood table 11ej, and user evaluation likelihood tables are also defined for other music genres. Hereinafter, the user evaluation likelihood tables 11ep, 11er, 11ej, . . . in the user evaluation likelihood table 11e will each be referred to as a "user evaluation likelihood table 11ex" unless particularly distinguished.

Referring back to FIG. 2, the RAM 12 is a memory for rewritably storing various pieces of work data, flags, and the like when the CPU 10 executes a program such as the control program 11a and includes a selected genre memory 12a in which a music genre selected by the performer is stored, a selected pattern memory 12b in which an estimated pattern is stored, a transition route memory 12c in which an estimated transition route Rm is stored, a tempo memory 12d, an IOI memory 12e in which a duration from the timing at which a previous key 2a is depressed to the timing at which a current key 2a is depressed (that is, a keying interval) is stored, a pitch likelihood table 12f, an accompaniment synchronization likelihood table 12g, an IOI likelihood table 12h, a likelihood table 12i, and a previous likelihood table 12j.

The tempo memory 12d is a memory in which the real time per beat of the accompaniment sound is stored. Hereinafter, the real time per beat of the accompaniment sound will be referred to as a "tempo," and the accompaniment sound is played on the basis of the tempo.

The pitch likelihood table 12f is a data table that stores a pitch likelihood which is a likelihood representing the relationship between the pitch of the performance information of the key 2a and the pitch of the state Jn. In the present embodiment, "1" is set as the pitch likelihood when the pitch of the performance information of the key 2a and the pitch of the state J in the input pattern table 11bx (FIG. 5(a)) perfectly match, "0.54" is set when the pitches partially match, and "0.4" is set when the pitches do not match. When the performance information of the key 2a has been input, the pitch likelihood is set for every state Jn.

FIG. 7(b) illustrates the case in which "do" has been input as the pitch of the performance information of the key 2a in the input pattern table 11br of the music genre "rock" of FIG. 5(a). Since the pitches of the state J1 and the state J74 in the input pattern table 11br is "do," "1" is set to the pitch likelihoods of the state J1 and the state J74 in the pitch likelihood table 12f. Further, since the pitch of the state J11 in the input pattern table 11br is a wildcard pitch, it is assumed that the pitches perfectly match no matter what pitch is input. Therefore, "1" is also set to the pitch likelihood of the state J11 in the pitch likelihood table 12f.

Since the pitch of the state J2 in the input pattern table 11br is "mi" and does not match the "do" of the pitch of the performance information of the key 2a, "0.4" is set for the state J2 in the pitch likelihood table 12f. In addition, since the pitch of the state J21 in the input pattern table 11br is "do & mi" and partially matches "do" of the pitch of the performance information of the key 2a, "0.54" is set for the state J21 in the pitch likelihood table 12f. A state Jn whose pitch is closest to the pitch of the performance information of the key 2a can be estimated on the basis of the pitch likelihood table 12f thus set.

Referring back to FIG. 2, the accompaniment synchronization likelihood table 12g is a data table that stores an accompaniment synchronization likelihood which is a likelihood representing the relationship between the timing in two bars at which the performance information of the key 2a has been input and the beat position B1 to B32 of the state Jn. The accompaniment synchronization likelihood table 12g will be described below with reference to FIG. 7(c).

FIG. 7(c) is a diagram schematically showing the accompaniment synchronization likelihood table 12g. As shown in FIG. 7(c), the accompaniment synchronization likelihood table 12g stores the accompaniment synchronization likelihood for each state Jn. In the present embodiment, the accompaniment synchronization likelihood is calculated from the difference between the timing in two bars at which the performance information of the key 2a has been input and the beat position B1 to B32 of the state Jn stored in the input pattern table 11bx on the basis of a Gaussian distribution of Equation (2) which will be described later.

Specifically, a great value of accompaniment synchronization likelihood is set for a state Jn of a beat position B1 to B32 having a small difference from the timing at which the performance information of the key 2a has been input. On the other hand, a small value of accompaniment synchronization likelihood is set for a state Jn of a beat position B1 to B32 having a great difference from the timing at which the performance information of the key 2a has been input. By estimating a state Jn for the performance information of the key 2a on the basis of the accompaniment synchronization likelihood of the accompaniment synchronization likelihood table 12g thus set, it is possible to estimate a state Jn of a beat position closest to the timing at which the performance information of the key 2a has been input.

Referring back to FIG. 2, the IOI likelihood table 12h is a data table that stores an IOI likelihood representing the relationship between the keying interval stored in the IOI memory 12e and the beat distance of the transition route Rm stored in the inter-transition route likelihood table 11dx. The IOI likelihood table 12h will be described below with reference to FIG. 8(a).

FIG. 8(a) is a diagram schematically showing the IOI likelihood table 12h. As shown in FIG. 8(a), the IOI likelihood table 12h stores the IOI likelihood for each transition route Rm. In the present embodiment, the IOI likelihood is calculated from the keying interval stored in the IOI memory 12e and the beat distance of the transition route Rm stored in the inter-transition route likelihood table 11dx according to Equation (1) which will be described later.

Specifically, a great value of IOI likelihood is set for a transition route Rm of a beat distance having a small difference from the keying interval stored in the IOI memory 12e. On the other hand, a small value of IOI likelihood is set for a transition route Rm of a beat distance having a great difference from the keying interval stored in the IOI memory 12e. By estimating a transition destination state Jn of a transition route Rm on the basis of the IOI likelihood of the transition route Rm thus set, it is possible to estimate a state Jn that is based on a transition route Rm whose beat distance is closest to the keying interval stored in the IOI memory 12e.

Referring back to FIG. 2, the likelihood table 12i is a data table that stores a likelihood obtained by combining the pattern transition likelihood, the miskeying likelihood, the user evaluation likelihood, the pitch likelihood, the accompaniment synchronization likelihood, and the IOI likelihood described above for each state Jn, and the previous likelihood table 12j is a data table that stores a previous value of the likelihood of each state Jn stored in the likelihood table 12i. The likelihood table 12i and the previous likelihood table 12j will be described below with reference to FIGS. 8(b) and 8(c).

FIG. 8(b) is a diagram schematically showing the likelihood table 12i and FIG. 8(c) is a diagram schematically showing the previous likelihood table 12j. As shown in FIG. 8(b), the likelihood table 12i stores results of combining the pattern transition likelihood, the miskeying likelihood, the user evaluation likelihood, the pitch likelihood, the accompaniment synchronization likelihood, and the IOI likelihood for each state Jn. Among these likelihoods, the pattern transition likelihood, the miskeying likelihood, and the IOI likelihood to be combined are those likelihoods of the transition route Rm corresponding to the transition destination state Jn and the user evaluation likelihood to be combined is the user evaluation likelihood of the pattern of the corresponding state Jn. The previous likelihood table 12i shown in FIG. 8(c) stores the likelihood of each state Jn that was obtained through combination and stored in the likelihood table 12i in previous processing.

Referring back to FIG. 2, the sound source 13 is a device that outputs waveform data corresponding to performance information input from the CPU 10. The DSP 14 is an arithmetic device for arithmetically processing the waveform data input from the sound source 13. Through the DSP 14, the effect of an output pattern designated by the selected pattern memory 12b is applied to the waveform data input from the sound source 13.

The DAC 16 is a conversion device that converts the waveform data input from the DSP 14 into analog waveform data. The amplifier 17 is an amplifying device that amplifies the analog waveform data output from the DAC 16 with a predetermined gain and the speaker 18 is an output device that emits (outputs) the analog waveform data amplified by the amplifier 17 as a musical sound.

Next, a main process executed by the CPU 10 will be described with reference to FIGS. 9 to 15. FIG. 9 is a flowchart of the main process. The main process is executed when the synthesizer 1 is powered on.

In the main process, first, a music genre selected by the performer is saved in the selected genre memory 12a (S1). Specifically, a music genre is selected by the performer's operation on a music genre selection button (not shown) of the synthesizer 1 and the type of the music genre is saved in the selected genre memory 12a.

It is to be noted that reference is made to an input pattern table 11bx, an output pattern table 11cx, an inter-transition route likelihood table 11dx, or a user evaluation likelihood table 11ex corresponding to the music genre stored in the selected genre memory 12a in the input pattern table 11b, the output pattern table 11c, the inter-transition route likelihood table 11d, or the user evaluation likelihood table 11e stored for each music genre, and hereinafter the "music genre stored in the selected genre memory 12a" will be referred to as a "corresponding music genre."

After the process of S1, it is checked whether or not a start instruction has been issued from the performer (S2). The start instruction is output to the CPU 10 when a start button (not shown) provided on the synthesizer 1 is selected. When no start instruction has been issued from the performer (S2: NO), the process of S2 is repeated to wait for a start instruction.

When a start instruction has been issued from the performer (S2: Yes), accompaniment starts on the basis of a first output pattern of the corresponding music genre (S3). Specifically, an accompaniment sound begins to be played on the basis of a drum pattern, a bass pattern, a chord progression, an arpeggio progression, an effect, a volume/velocity, and a timbre of the first output pattern (i.e., the output pattern of the pattern P1) in the output pattern table 11ex (FIG. 5(b)) of the corresponding music genre. Here, a tempo defined in the selected output pattern is stored in the tempo memory 12d and the accompaniment sound is played on the basis of the tempo.

After the process of S3, the pattern P1 is set in the selected pattern memory according to the start of the accompaniment sound by the process of S3 based on the output pattern of the pattern P1 in the music genre (S4).

After the process of S4, a user evaluation reflection process is executed (S5). Here, the user evaluation process will be described with reference to FIG. 10.

Figure 10:
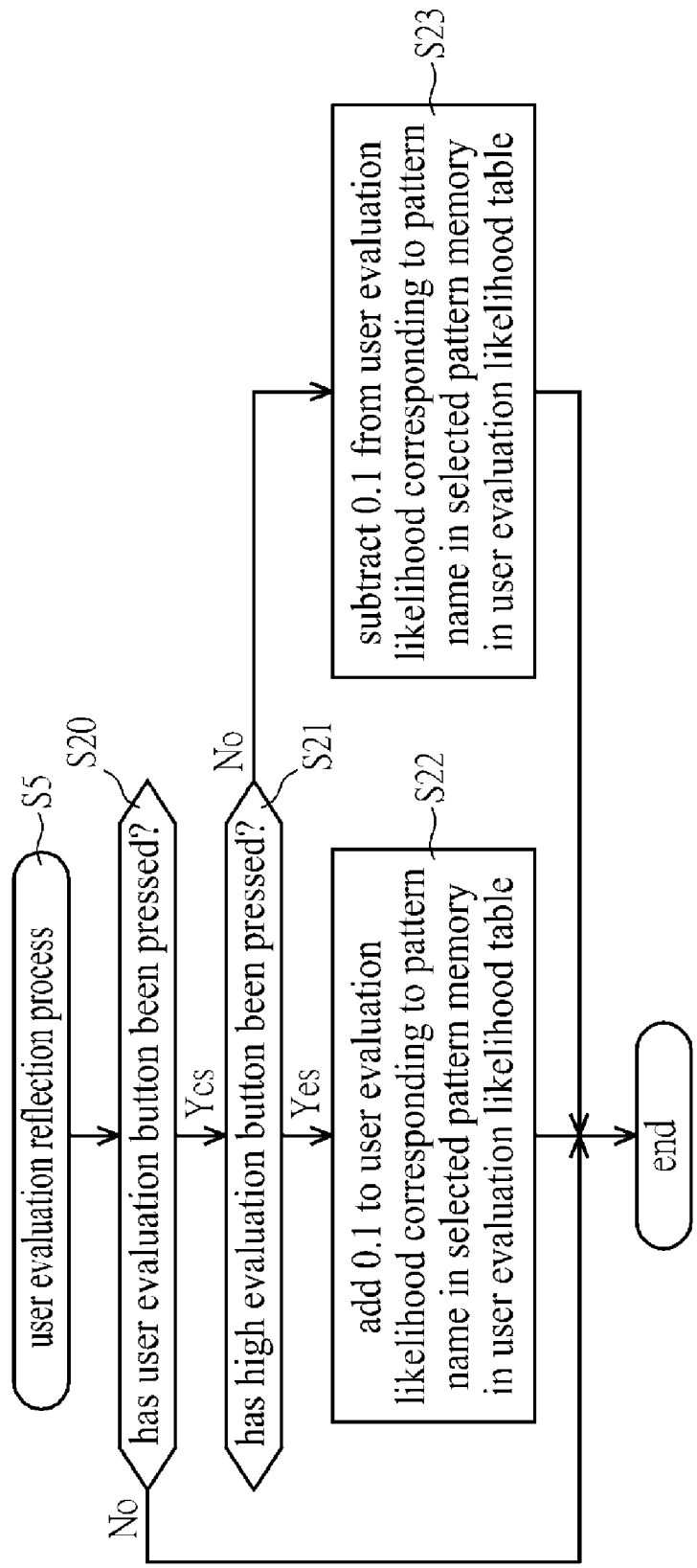
FIG. 10 is a flowchart of a user evaluation reflection process.

FIG. 10 is a flowchart of the user evaluation reflection process. In the user evaluation reflection process, first, it is checked whether or not a user evaluation button 3 (see FIG. 1) has been pressed (S20). When a user evaluation button 3 has been pressed (S20: Yes), it is further checked whether or not the high evaluation button 3a has been pressed (S21).

If it is determined in the process of S21 that the high evaluation button 3a has been pressed (S21: Yes), 0.1 is added to a user evaluation likelihood corresponding to the pattern stored in the selected pattern memory 12b in the user evaluation likelihood table 11e (S22). In the process of S22, if the user evaluation likelihood after the addition is greater than 1, 1 is set to the user evaluation likelihood.

On the other hand, if it is determined in the process of S21 that the low evaluation button 3b has been pressed (S21: No), 0.1 is subtracted from the user evaluation likelihood corresponding to the pattern stored in the selected pattern memory 12b in the user evaluation likelihood table 11e (S23). In the process of S23, if the user evaluation likelihood after the subtraction is smaller than 0, 0 is set to the user evaluation likelihood.

If it is determined in the process of S20 that no user evaluation buttons 3 have been pressed (S20: No), the processes of S21 to S23 are skipped. After the processes of S20, S22, and S23, the user evaluation reflection process is terminated and the processing returns to the main process.

Referring back to FIG. 9, after the user evaluation reflection process of S5, it is checked whether or not a key input has been made, that is, performance information of a key 2a has been input (S6). If it is determined in the process of S6 that performance information of a key 2a has been input (S6: Yes), an input pattern search process is executed (S7). Here, the input pattern search process will be described with reference to FIGS. 11 to 15.

Figure 11:
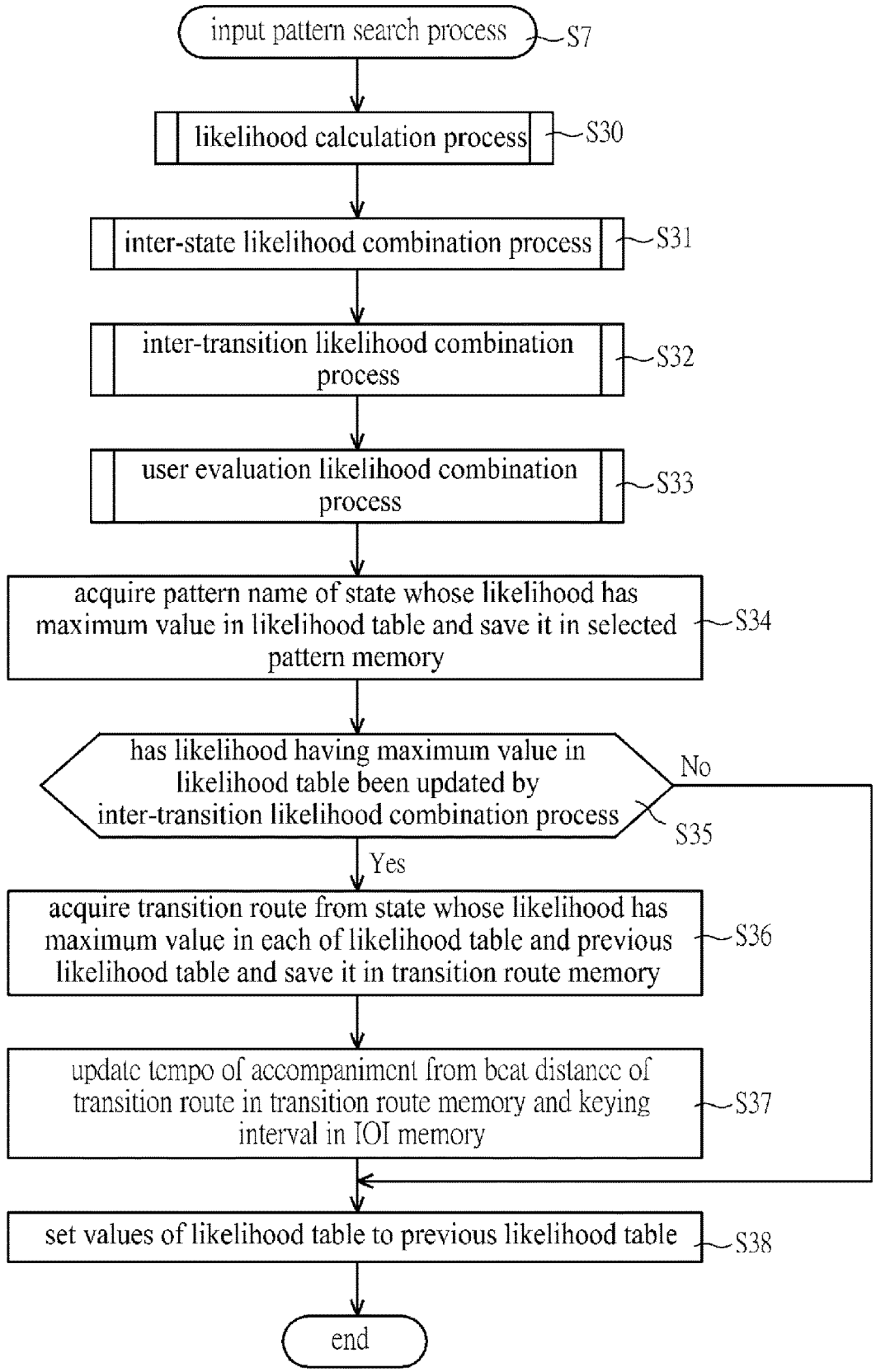
FIG. 11 is a flowchart of an input pattern search process.

FIG. 11 is a flowchart of the input pattern search process. In the input pattern search process, first, a likelihood calculation process is executed (S30). The likelihood calculation process will be described below with reference to FIG. 12.

Figure 12:
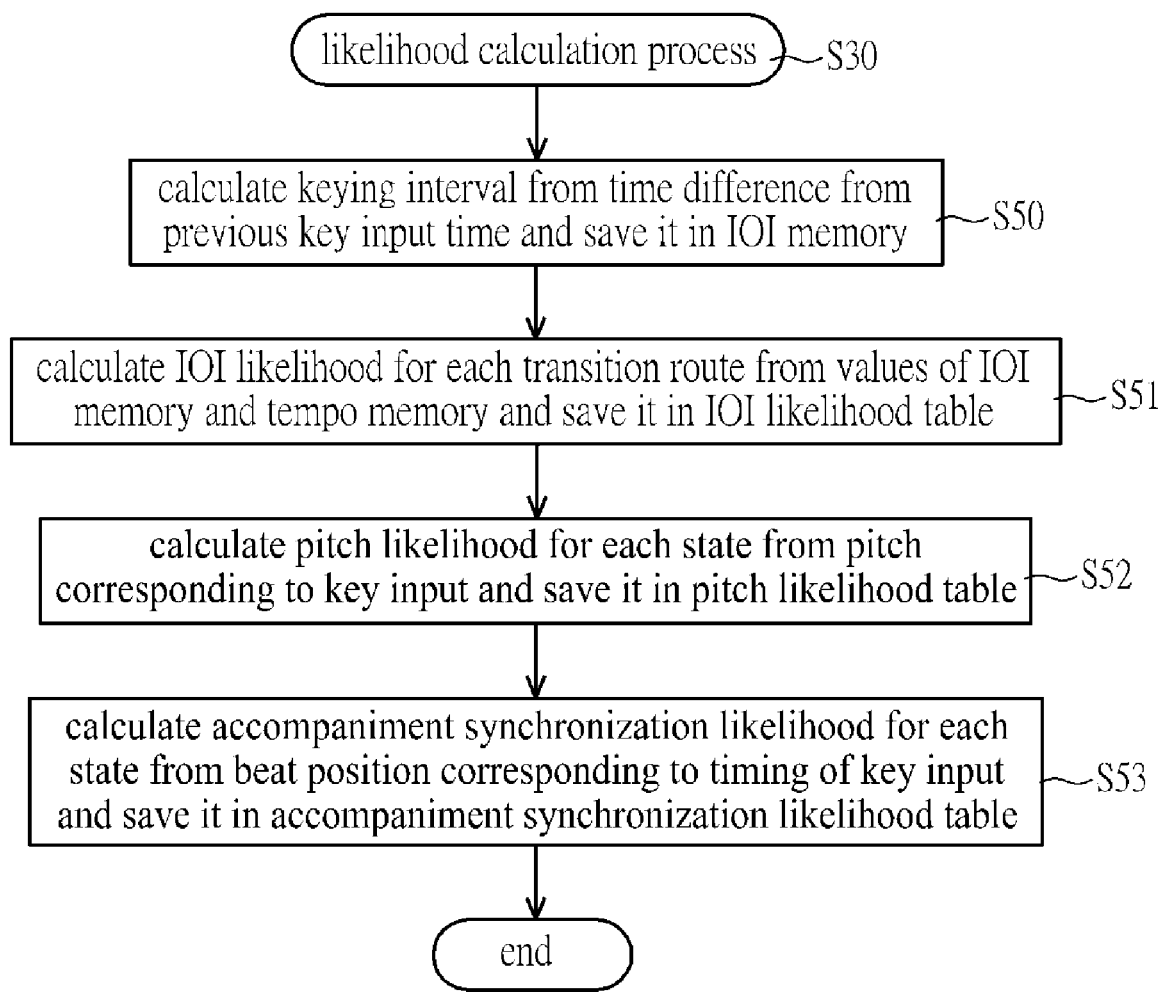
FIG. 12 is a flowchart of a likelihood calculation process.

FIG. 12 is a flowchart of the likelihood calculation process. In the likelihood calculation process, first, the time difference between input of performance information of keys 2a, that is, the keying interval, is calculated from the difference between the time at which performance information of a previous key 2a is input and the time at which performance information of a current key 2a is input, and the calculated keying interval is saved in the IOI memory 12e (S50).

After the process of S50, an IOI likelihood is calculated from the keying interval in the IOI memory 12e, the tempo in the tempo memory 12d, and the beat distance of each transition route Rm in the inter-transition route likelihood table 11dx of the corresponding music genre, and the calculated IOI likelihood is saved in the IOI likelihood table 12h (S51). Specifically, letting x be the keying interval in the IOI memory 12e, Vm be the tempo in the tempo memory 12d, and $\Delta\tau$ be the beat distance of a transition route Rm stored in the inter-transition route likelihood table 11dx, an IOI likelihood G is calculated by a Gaussian distribution of Equation (1).

$$G = \frac{1}{\sqrt{2\pi\sigma^2}} \exp\left(-\frac{\left(\frac{x}{Vm} - \Delta\tau\right)^2}{2\sigma^2}\right) \quad (1)$$

Here, $\sigma$ is a constant representing the standard deviation in the Gaussian distribution of Equation (1) and is set to a value calculated in advance through experiments or the like. This IOI likelihood G is calculated for all transition routes Rm and the results are stored in the IOI likelihood table 12h. That is, since the IOI likelihood G follows the Gaussian distribution of Equation (1), a greater value of IOI likelihood G is set for the transition route Rm as the beat distance of the transition route Rm has a smaller difference from the keying interval in the IOI memory 12e.

After the process of S51, the pitch likelihood is calculated for each state Jn from the pitch of the performance information of the key 2a, and the calculated pitch likelihood is saved in the pitch likelihood table 12f (S52). As described above with reference to FIG. 7(b), the pitch of the performance information of the key 2a is compared with the pitch of each state Jn in the input music pattern table 11bx of the corresponding music genre and then "1" is set to the pitch likelihood of each state Jn, whose pitch perfectly matches the pitch of the performance information, in the pitch likelihood table 12f, "0.54" is set to the pitch likelihood of each state Jn, whose pitch partially matches it, in the pitch likelihood table 12f, and "0.4" is set to the pitch likelihood of for each state Jn, whose pitch does not match it, in the pitch likelihood table 12f.

After the process of S52, the accompaniment synchronization likelihood is calculated from a beat position corresponding to the time at which the performance information of the key 2a has been input and the beat position in the input music pattern table 11bx of the corresponding music genre, and the calculated accompaniment synchronization likelihood is saved in the accompaniment synchronization likelihood table 12g (S53). Specifically, letting tp be a beat position in a unit of two bars into which the time at which the performance information of the key 2a has been input is converted and $\tau$ be the beat position in the input pattern table 11bx of the corresponding music genre, an accompaniment synchronization likelihood B is calculated by a Gaussian distribution of Equation (2).

$$B = \frac{1}{\sqrt{2\pi\rho^2}} \exp\left(-\frac{(tp - \tau)^2}{2\rho^2}\right) \quad (2)$$

Here, $\rho$ is a constant representing the standard deviation in the Gaussian distribution of Equation (2) and is set to a value calculated in advance through experiments or the like.

This accompaniment synchronization likelihood B is calculated for all states Jn and the results are stored in the accompaniment synchronization likelihood table 12g. That is, since the accompaniment synchronization likelihood B follows the Gaussian distribution of Equation (2), a greater value of accompaniment synchronization likelihood B is set for the state Jn as the beat distance of the state Jn has a smaller difference from the beat position corresponding to the time at which the performance information of the key 2a has been input.

After the process of S53, the likelihood calculation process is terminated and the processing returns to the input pattern search process of FIG. 11.

Referring back to FIG. 11, after the likelihood calculation process of S30, an inter-state likelihood combination process is executed (S31). Here, the inter-state likelihood combination process will be described with reference to FIG. 13.

Figure 13:
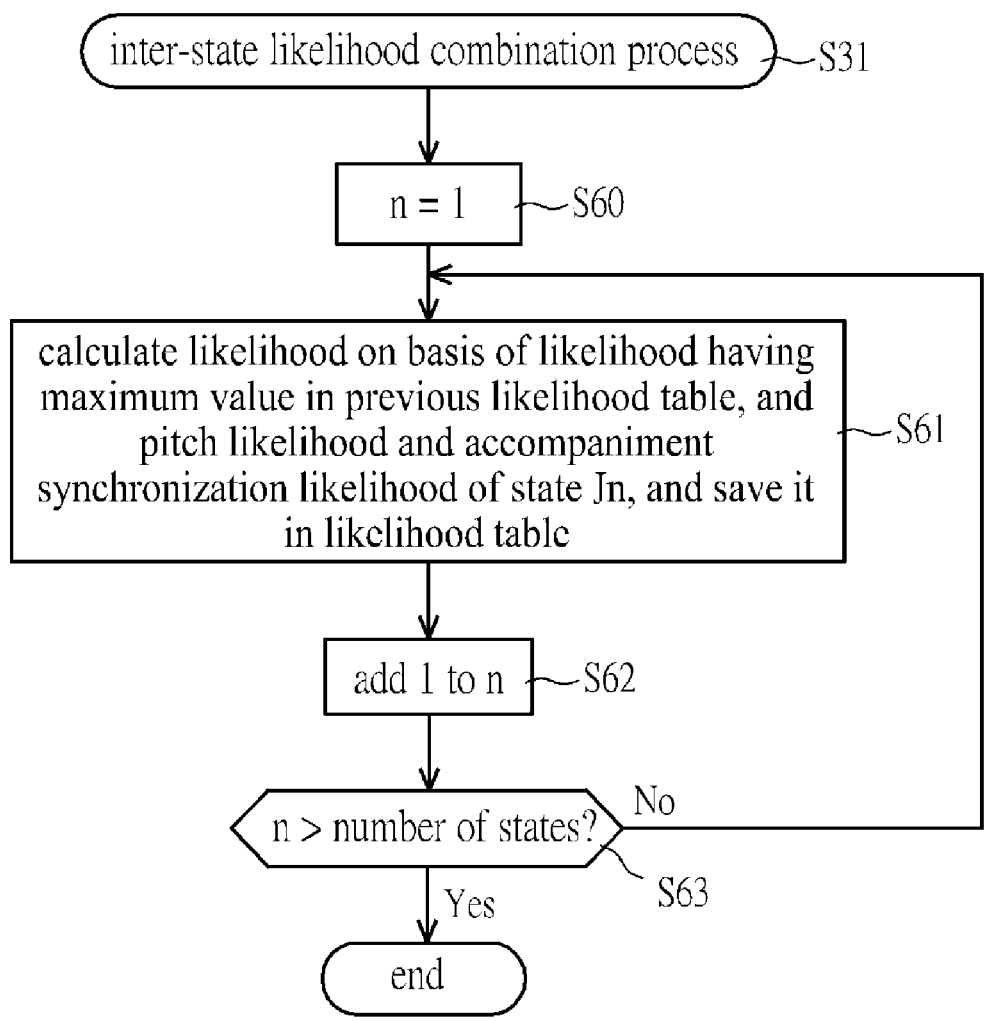
FIG. 13 is a flowchart of an inter-state likelihood combination process.

FIG. 13 is a flowchart of the inter-state likelihood combination process. This inter-state likelihood combination process is a process for calculating a likelihood for each state Jn from each likelihood calculated in the likelihood calculation process in FIG. 12. In the inter-state likelihood combination process, first, 1 is set to a counter variable n (S60). Hereinafter, "n" in the "state Jn" in the inter-state likelihood combination process represents the counter variable n. For example, when the counter variable n is 1, the state Jn represents the "state J1."

After the process of S60, the likelihood of the state Jn is calculated from the maximum value of the likelihood stored in the previous likelihood table 12j, the pitch likelihood of the state Jn in the pitch likelihood table 12f, and the accompaniment synchronization likelihood of the state Jn in the accompaniment synchronization likelihood table 12g, and the calculated likelihood is saved in the likelihood table 12i (S61). Specifically, letting Lp_M be the maximum value of the likelihood stored in the previous likelihood table 12j, Pi_n be the pitch likelihood of the state Jn in the pitch likelihood table 12f, and B_n be the accompaniment synchronization likelihood of the state Jn in the accompaniment synchronization likelihood table 12g, a logarithmic likelihood log(L_n) which is the logarithm of the likelihood L_n of the state Jn is calculated by a Viterbi algorithm of Equation (3).

$$\log(L\_n)=\log(Lp\_M)+\log(Pi\_n)+\log(\alpha \cdot B\_n) \quad (3)$$

Here, α is a penalty constant for the accompaniment synchronization likelihood Bn, that is, a constant considering the case of not transitioning to the state Jn, and is set to a value calculated in advance through experiments or the like. The likelihood L_n obtained by removing the logarithm from the logarithmic likelihood log(L_n) calculated by Equation (3) is stored in a memory area corresponding to the state Jn in the likelihood table 12i.

The likelihood L_n is calculated by the product of the maximum value LpM of the likelihood stored in the previous likelihood table 12j, the pitch likelihood Pi_n, and the accompaniment synchronization likelihood Bn. Here, since each of the likelihoods has a value of 0 or more and 1 or less, there is a fear that multiplication of the likelihoods may cause an underflow. Therefore, by taking logarithms for the likelihoods Lp_M, Pi_n and B_n, it is possible to convert the calculation of the product of the likelihoods Lp_M, Pi_n, and B_n into the calculation of the sum of the logarithms of the likelihoods Lp_M, Pi_n, and B_n. Then, by removing the logarithm from the logarithmic likelihood log(L_n), which is the result of the calculation, to calculate the likelihood L_n, it is possible to obtain a highly accurate likelihood L_n with the underflow prevented.

After S61, 1 is added to the counter variable n (S62) and it is checked whether or not the counter variable n after the addition is greater than the number of states Jn (S63). If it is determined in the process of S63 that the counter variable n is equal to or less than the number of states Jn, the processes from S61 onward are repeated. On the other hand, if it is determined that the counter variable n is greater than the number of states Jn (S63: Yes), the inter-state likelihood combination process is terminated and the processing returns to the input pattern search process of FIG. 11.

Referring back to FIG. 11, after the inter-state likelihood combination process of S31, an inter-transition likelihood combination process is executed (S32). The inter-transition likelihood combination process will be described below with reference to FIG. 14.

Figure 14:
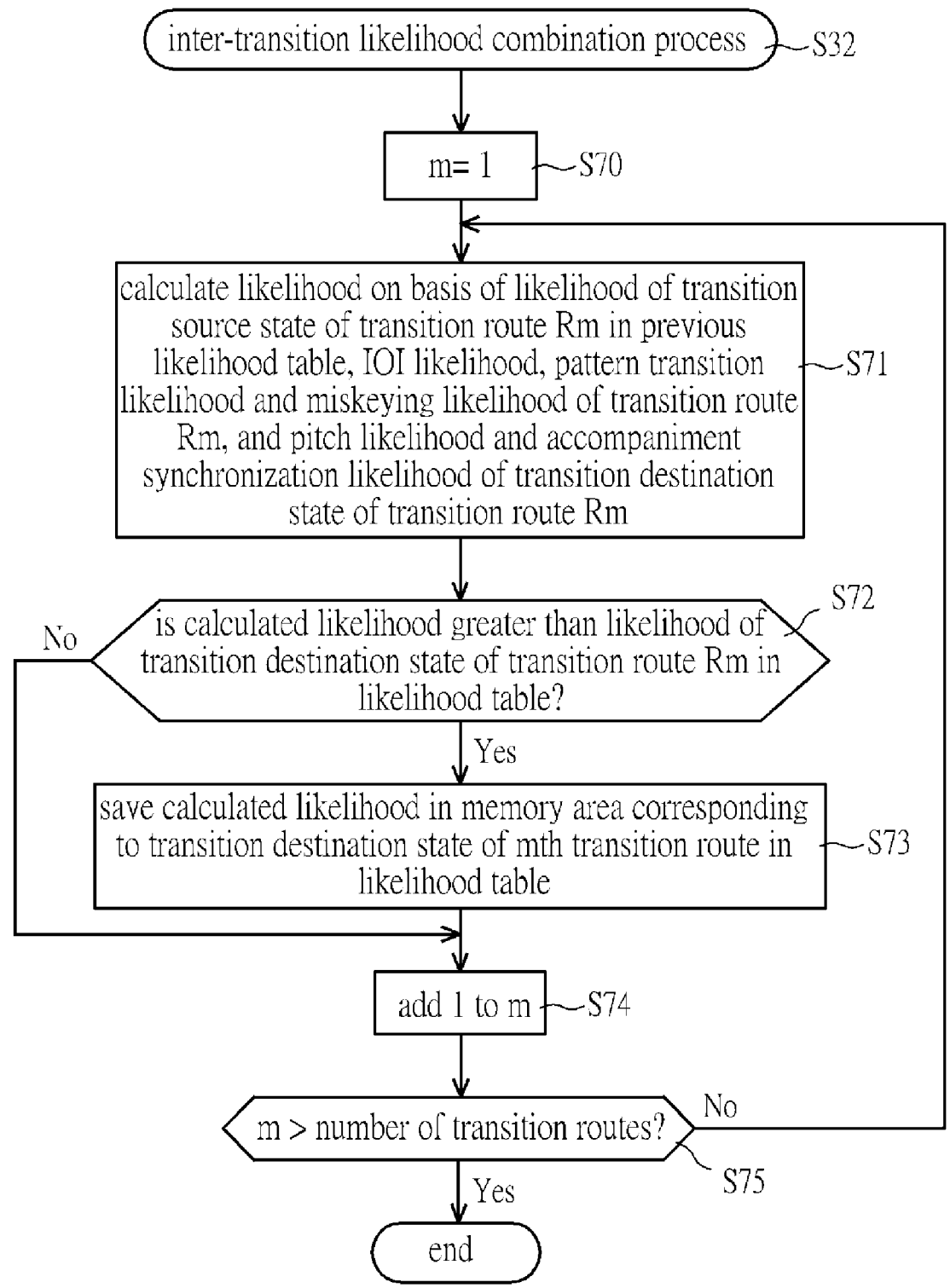
FIG. 14 is a flowchart of an inter-transition likelihood combination process.

FIG. 14 is a flowchart of the inter-transition likelihood combination process. The inter-transition likelihood combination process is a process for calculating a likelihood of the transition destination state Jn of each transition route Rm from each likelihood calculated in the likelihood calculation process of FIG. 12 and the pattern transition likelihood and the miskeying likelihood of the preset inter-transition route likelihood table 11d.

In the inter-transition likelihood combination process, first, 1 is set to a counter variable m (S70). Hereinafter, "m" in the "transition route Rm" in the inter-transition likelihood combination process represents the counter variable m. For example, when the counter variable m is 1, the transition route Rm represents the "transition route R1."

After the process of S70, a likelihood is calculated on the basis of the likelihood of the transition source state Jn of the transition route Rm in the previous likelihood table 12i, the IOI likelihood of the transition route Rm in the IOI likelihood table 12h, the pattern transition likelihood and the miskeying likelihood in the inter-transition route likelihood table 11dx of the corresponding music genre, the pitch likelihood of the transition destination state Jn of the transition route Rm in the pitch likelihood table 12f, and the accompaniment synchronization likelihood of the transition destination state Jn of the transition route Rm in the accompaniment synchronization likelihood table 12g (S71).

Specifically, letting Lp_mb be the previous likelihood of the transition source state Jn of the transition route Rm in the previous likelihood table 12j, I_m be the IOI likelihood of the transition route Rm in the IOI likelihood table 12h, Ps_m the pattern transition likelihood in the inter-likelihood table 11dx of the corresponding music genre, Ms_m be the miskeying likelihood in the inter-transition route likelihood table 11dx of the corresponding music genre, Pi_mf be the pitch likelihood of the transition destination state Jn of the transition route Rm in the pitch likelihood table 12f, and B_mf be the accompaniment synchronization likelihood of the transition destination state Jn of the transition route Rm in the accompaniment synchronization likelihood table 12g, a logarithmic likelihood log(L), which is the logarithm of the likelihood L, is calculated by a Viterbi algorithm of Equation (4).

$$\log(L)=\log(Lp\_mb)+\log(I\_m)+\log(Ps\_m)+\log(Ms\_m)+\log(Pi\_mf)+\log(B\_mf) \quad (4)$$

Here, the purpose of calculating the logarithmic likelihood log(L) by the sum of the logarithms of the likelihoods Lp_mb, I_m, Ps_m, Ms_m, Pi_mf, and B_mf in Equation (4) is to prevent underflow for the likelihood L, similar to the above Equation (3). Then, the likelihood L is calculated by removing the logarithm from the logarithmic likelihood log(L) calculated through the above Equation (4).

After the process of S71, it is checked whether or not the likelihood L calculated in the process of S70 is greater than the likelihood of the transition destination state Jn of the transition route Rm in the likelihood table 12$i$ (S72). If it is determined in the process of S72 that the likelihood L calculated in the process of S70 is greater than the likelihood of the transition destination state Jn of the transition route Rm in the likelihood table 12$i$, the likelihood L calculated in the process of S70 is saved in a memory area corresponding to the transition destination state Jn of the transition route Rm in the likelihood table 12$i$ (S73).

On the other hand, if it is determined in the process of S72 that the likelihood L calculated in the process of S70 is equal to or less than the likelihood of the transition destination state Jn of the transition route Rm in the likelihood table 12$i$ (S72: No), the process of S73 is skipped.

After the processes of S72 and S73, 1 is added to the counter variable m (S74) and thereafter it is checked whether or not the counter variable m is greater than the number of transition routes Rm (S75). If it is determined in the process of S75 that the counter variable m is equal to or less than the number of transition routes Rm (S75: No), the processes from S71 onward are repeated and, if it is determined in the process of S75 that the counter variable m is greater than the number of transition routes Rm (S75: Yes), the inter-transition likelihood combination process is terminated and the processing returns to the input pattern search process of FIG. 11.

That is, in the inter-transition likelihood combination process, the likelihood for the transition destination state Jn in the transition route Rm is calculated with reference to the previous likelihood Lp_mb of the transition source state Jn of the transition route Rm in the previous likelihood table 12$j$. This is because the transition of the state Jn depends on the transition source state Jn. That is, the probability that a state Jn whose previous likelihood Lp_mb is great is a transition source state Jn at the current time is estimated to be high, and conversely the probability that a state Jn whose previous likelihood Lp_mb is small is a transition source state Jn at the current time is estimated to be low. Therefore, by calculating the likelihood for the transition destination state Jn in the transition route Rm with reference to the previous likelihood Lp_mb, it is possible to obtain a highly accurate likelihood taking into consideration the transition relation between states Jn.

On the other hand, since the likelihood calculated in the inter-transition likelihood combination process depends on the transition relation between states Jn, it is also possible to consider cases in which the transition source state Jn and the transition destination state Jn do not correspond to those of the input pattern table 11$bx$ of the corresponding music genre, for example, such as when performance information of the keyboard 2 is input immediately after performance of the accompaniment starts or when the input interval of performance information of the keyboard 2 is significantly great. In such cases, likelihoods calculated on the basis of the transition relation between states Jn in the inter-transition likelihood combination process have all small values.

Here, in the inter-state likelihood combination process described above with reference to FIG. 13, the likelihood is calculated from the pitch likelihood and the accompaniment synchronization likelihood set for each state Jn and therefore it does not depend on the transition route Rm. Therefore, when the transition source state Jn and the transition destination state Jn do not correspond to those of the input pattern table 11$bx$ of the corresponding music genre, the likelihood of the state Jn calculated in inter-state likelihood combination process is greater than the likelihood of the state Jn calculated in the inter-transition likelihood combination process. In this case, the likelihood calculated in the inter-state likelihood combination process remains stored in the likelihood table 12$i$.

Therefore, no matter whether there is a transition relation between states Jn, it is possible to appropriately calculate the likelihood of the state Jn according to each case, by combining a likelihood calculation based on the previous likelihood Lp_mb through the inter-transition likelihood combination process and a likelihood calculation based on the performance information of the key 2$a$ at that point in time through the inter-state likelihood combination process.

Referring back to FIG. 11, after the inter-transition likelihood combination process of S32, a user evaluation likelihood combination process is executed (S33). Here, the user evaluation likelihood combination process will be described with reference to FIG. 15.

Figure 15:
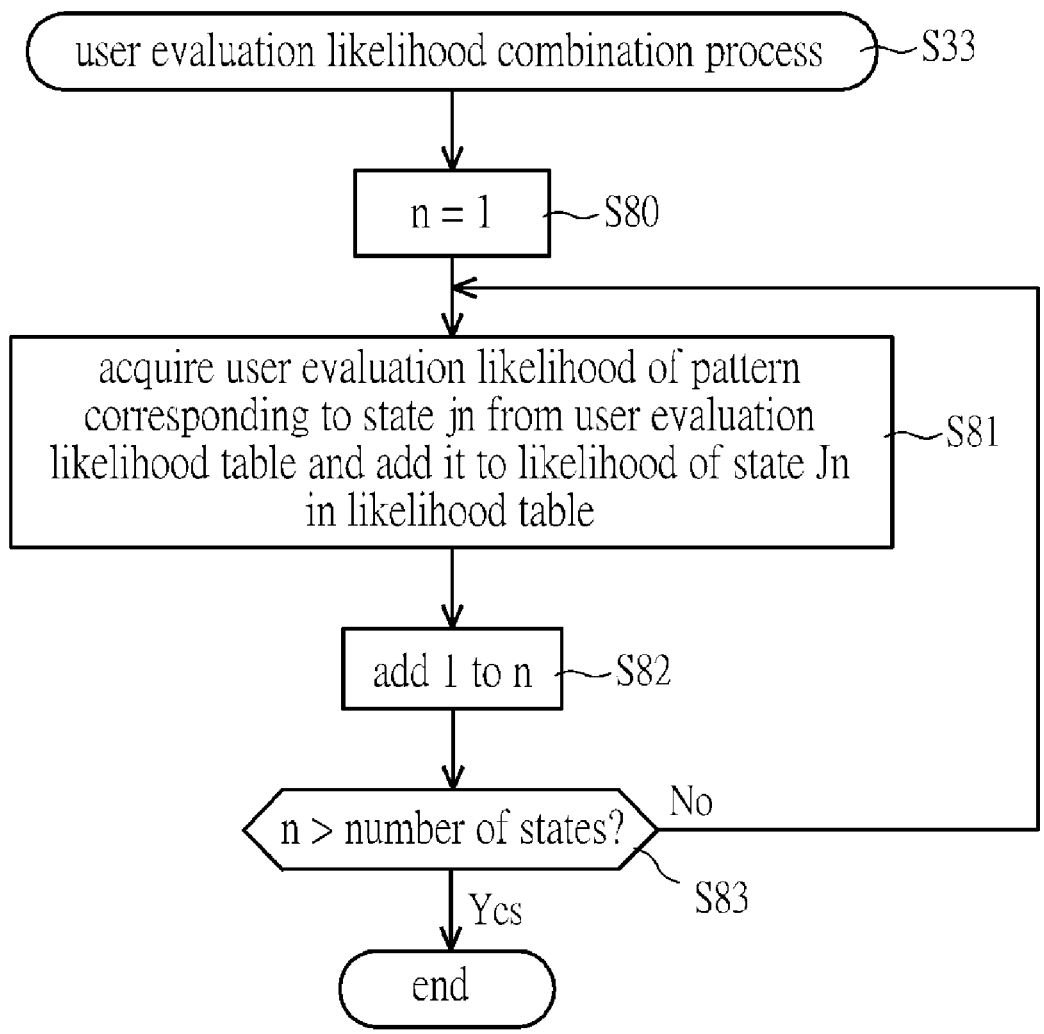
FIG. 15 is a flowchart of a user evaluation likelihood combination process.

FIG. 15 is a flowchart of the user evaluation likelihood combination process. In the user evaluation likelihood combination process, first, 1 is set to the counter variable n (S80). Hereinafter, in the user evaluation likelihood combination process, "n" in the "state Jn" represents the counter variable n, similar to the inter-state likelihood combination process of FIG. 13. For example, when the counter variable n is 1, the state Jn represents the "state J1."

After the process of S80, a user evaluation likelihood of a pattern corresponding to the state Jn is acquired from the user evaluation likelihood table 11$e$ and added to the likelihood of the state Jn in the likelihood table 12$i$ (S81). After the process of S81, 1 is added to the counter variable n (S82) and it is checked whether or not the counter variable n is greater than the total number of states Jn (S83). If it is determined in the process of S83 that the counter variable n is equal to or less than the total number of states Jn (S83: No), the processes from S81 onward are repeated. On the other hand, if it is determined that the counter variable n is greater than the total number of states Jn (S83: Yes), the user evaluation likelihood combination process is terminated and the processing returns to the input pattern search process of FIG. 11.

By the user evaluation likelihood combination process, the user evaluation likelihood is reflected in the likelihood table 12$i$. That is, the performer's evaluation on the output pattern is reflected in the likelihood table 12$i$. Thus, the likelihood of the state Jn in the likelihood table 12$i$ increases as the performer's evaluation on the output pattern of the state Jn increases and therefore the estimated output pattern can be based on the performer's evaluation.

Referring back to FIG. 11, after the user evaluation combination process of S33, a state Jn whose likelihood has the maximum value in the likelihood table 12$i$ is acquired, a pattern corresponding to the state Jn is acquired from the input pattern table 11$bx$ of the corresponding music genre, and the acquired pattern is saved in the selected pattern memory 12$b$ (S34). That is, a state Jn most likely for the performance information of the key 2$a$ is acquired from the likelihood table 12$i$ and a pattern corresponding to the state Jn is acquired. In this way, it is possible to select a pattern most likely for the performance information of the key 2$a$.

After the process of S34, it is checked whether or not the likelihood having the maximum value in the likelihood table 12$i$ has been updated by the inter-transition likelihood combination process of S32 (S35). That is, it is checked whether or not the likelihood of the state Jn used to determine the pattern in the process of S34 has been updated with the likelihood based on the previous likelihood Lp_mb by the processes of S71 to S73 in FIG. 14.

In the process of S35, when the likelihood having the maximum value in the likelihood table 12i has been updated by the inter-transition likelihood combination process (S35: Yes), a current transition route Rm is acquired from the state Jn whose likelihood has the maximum value in the likelihood table 12i and a state Jn whose likelihood has the maximum value in the previous likelihood table 12j and the acquired current transition route Rm is saved in the transition route memory 12c (S36). Specifically, the state Jn whose likelihood has the maximum value in the likelihood table 12i and the state Jn whose likelihood has the maximum value in the previous likelihood table 12j are searched for in the transition source states Jn and the transition destination states Jn in the inter-transition route table of the corresponding music genre, and a transition route Rm whose states Jn match them is acquired from the inter-transition route likelihood table 11dx of the corresponding music genre and saved in the transition route memory 12c.

After the process of S36, a tempo is calculated from the beat distance of the transition route Rm in the transition route memory 12c and the keying interval in the IOI memory 12e, and the calculated tempo is saved in the tempo memory 12d (S37). Specifically, letting Δτ be the beat distance of the transition route Rm in the inter-transition route likelihood table 11dx of the corresponding music genre, which matches the transition route Rm in the transition route memory 12c, x be the keying interval in the IOI memory 12e, and Vmb be the current tempo stored in the tempo memory 12d, the updated tempo Vm is calculated by Equation (5).

$$Vm = \gamma \cdot \frac{x}{\Delta\tau} + (1-\gamma) \cdot Vmb \quad (5)$$

Here, γ is a constant of 0<γ<1, which is a value preset through experiments or the like.

That is, since the likelihood having the maximum value in the likelihood table 12i used to determine the pattern in the process of S34 has been updated by the inter-transition likelihood combination process of S32, it is estimated that the previous and current inputs of keys 2a correspond to the transition of a transition route Rm between a state Jn whose likelihood has the maximum value in the previous likelihood table 12j and a state Jn whose likelihood has the maximum value in the likelihood table 12i.

Therefore, by changing the tempo of the accompaniment sound from the beat distance of the transition route Rm and the keying interval between the previous and current inputs of keys 2a, it is possible to provide an accompaniment sound with less discomfort based on the keying interval of keys 2a of the actual performer.

If it is determined in the process of S35 that the likelihood having the maximum value in the likelihood table 12i has not been updated by the inter-transition likelihood combination process (S35: No), the processes of S36 and S37 are skipped. That is, in such a case, since the likelihood having the maximum value in the likelihood table 12i is that calculated by the inter-state combination process of S31, it is estimated that the state Jn whose likelihood has the maximum value does not depend on the transition route Rm.

In this case, even if searching of the transition route Rm using states Jn in the process of S36 is performed, there is a fear that it may not be possible to acquire the matching transition route Rm, or even if the transition route Rm can be acquired, there is also a fear that an incorrect transition route Rm may be acquired. In such a state in which it is not possible to correctly acquire the transition route Rm, even if the tempo update process of S37 is performed, there is a fear that the calculated tempo may be incorrect. Since the likelihood having the maximum value in the likelihood table 12i has not been updated by the inter-transition likelihood combination process, it is possible to prevent an incorrect tempo from being applied to the accompaniment sound by skipping the processes of S36 and S37.

After the processes of S35 and S37, the values in the likelihood table 12i are set to the previous likelihood table 12j (S38). After the process of S38, the input pattern search process is terminated and the processing returns to the main process of FIG. 9.

Referring back to FIG. 9, after the input pattern search process of S7, the accompaniment sound is changed on the basis of the pattern in the selected pattern memory 12b and the output pattern table 11cx of the corresponding music genre (S8). Specifically, the accompaniment sound is changed on the basis of a drum pattern, a bass pattern, a chord progression, and an arpeggio progression, which correspond to the pattern in the selected pattern memory 12b, in the output pattern table 11cx of the corresponding music genre. At this time, when the tempo has been updated in the process of S37 in the input pattern search process (FIG. 11), the tempo of the accompaniment sound is also set to the tempo of the updated tempo memory 12d.

That is, every time performance information of a key 2a is input, a state Jn most likely for the performance information is estimated and an accompaniment sound and an effect based on an output pattern corresponding to the state Jn are output. Thus, in accordance with the performer's free performance, it is possible to switch to and output an accompaniment sound and an effect suitable for the performance. Further, since it is unnecessary for the performer to operate the synthesizer 1 with respect to such switching, usability of the synthesizer 1 for the performer is improved and it is possible for the performer to concentrate more on performance operations on the keys 2a or the like.

After the process of S8, a musical sound is output on the basis of the performance information of the key 2a (S9). At this time, the timbre of the musical sound based on the performance information of the key 2a is set to the timbre corresponding to the pattern in the selected pattern memory 12b in the output pattern table 11cx of the corresponding music genre and the musical sound is output with the volume/velocity and the effect corresponding to the pattern in the selected pattern memory 12b in the output pattern table 11cx of the corresponding music genre being applied to the musical sound. Here, the effect is applied to the musical sound based on the performance information of the key 2a through processing of waveform data of such a musical sound output from the sound source 13 by the DSP 14. After the process of S9, the processes from S5 onward are repeated.

If it is determined in the process of S6 that performance information of a key 2a has not been input (S6: No), it is further checked whether or not performance information of a key 2a has not been input over six or more bars (S10). If it is determined in the process of S10 that performance information of a key 2a has not been input over six or more bars (S10: Yes), the processing shifts to an ending part of the corresponding music genre (S11). That is, if performance information of a key 2a has not been input over six or more bars, it is estimated that the performance has ended. In such a case, by shifting to the ending part of the corresponding music genre, it is possible to shift to the ending part without the performer operating the synthesizer 1.

After the process of S11, during the performance of the ending pattern, it is checked whether or not performance information of a key 2a has been input (S12). If it is determined in the process of S12 that performance information of a key 2a has been input, it is estimated that performance of the performer has been resumed, and therefore a shift is made from the ending part to an accompaniment sound immediately before shifting to the ending part (S14) and a musical sound is output on the basis of the performance information of the key 2a (S15). After the process of S15, the processes from S5 onward are repeated.

If it is determined in the process of S12 that performance information of a key 2a has not been input during the performance of the ending part (S12: No), it is checked whether or not the performance of the ending part has ended (S13). If it is determined in the process of S13 that the performance of the ending part has ended (S13: Yes), it is estimated that the performer's performance has completely ended, and thus the processes from S1 onward are repeated. On the other hand, if it is determined in the process of S13 that the performance of the ending part has not ended (S13: No), the processes from S12 onward are repeated.

Although the disclosure has been described on the basis of the above embodiment, it can be easily inferred that various improvements and modifications are possible.

In the above embodiment, the synthesizer 1 is illustrated as an automatic performance device. However, the disclosure is not necessarily limited thereto and may be applied to an electronic musical instrument that outputs an accompaniment sound and an effect together with a musical sound generated by the performer's performance, such as an electronic organ and an electronic piano.

In the above embodiment, a drum pattern, a bass pattern, a chord progression, an arpeggio progression, an effect, a volume/velocity and a timbre are set as an output pattern. However, the disclosure is not necessarily limited thereto and may be configured such that a music expression other than a drum pattern, a bass pattern, a chord progression, an arpeggio progression, an effect, a volume/velocity and a timbre, for example, a rhythm pattern other than drums and basses or audio data such as human singing voice is added to the output pattern.

In the above embodiment, when the output pattern is switched, the drum pattern, the bass pattern, the chord progression, the arpeggio progression, the effect, the volume/velocity and the timbre of the output pattern are all switched. However, the disclosure is not necessarily limited thereto and may be configured such that only some of the drum pattern, the bass pattern, the chord progression, the arpeggio progression, the effect, the volume/velocity and the timbre of the output pattern (for example, the drum pattern and the chord progression only) are switched.

The disclosure may also be configured such that, for each output pattern, elements of the output pattern which are to be switched are preset and, when an output pattern is switched, only the set output pattern is to be switched. Thereby, output patterns can be made according to the performer's preferences.

The above embodiment is configured such that the pitch likelihood and the accompaniment synchronization likelihood are calculated for all states Jn in the processes of S52 and S53 of FIG. 12. However, the disclosure is not limited thereto and may be configured such that the pitch likelihood and the accompaniment synchronization likelihood are calculated for some states Jn. For example, the disclosure may be configured such that the pitch likelihood and the accompaniment synchronization likelihood are calculated only for a state Jn which is a transition destination of a transition route Rm whose transition source is a state Jn whose likelihood has the maximum value in the previous likelihood table 12j.

In the above embodiment, the playing duration of the accompaniment sound of each output pattern has a length of two bars in common time. However, the disclosure is not limited thereto and the playing duration of the accompaniment sound may one bar or may be three or more bars. Also, the meter of the accompaniment sound is not limited to common time and the disclosure may be configured such that another meter such as three-four time or six-eight time is used as appropriate.

The above embodiment is configured such that a transition route due to sound skipping which transitions from a state Jn that was two states ago in the same pattern is set as a transition route to a state Jn in the same pattern. However, the disclosure is not limited thereto and may be configured such that a transition route which transitions from a state Jn that was three or more states ago in the same pattern is included as a transition route due to sound skipping. The disclosure may also be configured such that a transition route due to sound skipping is omitted from transition routes to states Jn in the same pattern.

The above embodiment is also configured such that transition routes where a transition source state Jn of a different pattern is immediately prior to the beat position of a transition destination state Jn are set as transition routes to states Jn in different patterns. However, the disclosure is not necessarily limited thereto and may be configured such that a transition route due to sound skipping which transitions from a state Jn that was two or more states ago which is a transition source in a different pattern is also set as a transition route to a state Jn in a different pattern.

The above embodiment is configured such that the IOI likelihood G and the accompaniment synchronization likelihood B follow the Gaussian distributions of Equation (1) and Equation (2), respectively. However, the disclosure is not limited thereto and may be configured such that the IOI likelihood G follows another probability distribution function such as a Laplacian distribution.

The above embodiment is configured such that, in the process of S61 of FIG. 13, the likelihood $L\_n$ obtained by removing the logarithm from the logarithmic likelihood $\log(L\_n)$ calculated by Equation (3) is stored in the likelihood table 12i and, in the processes of S71 to S73 of FIG. 14, the likelihood L obtained by removing the logarithm from the logarithmic likelihood $\log(L)$ calculated by Equation (4) is stored in the likelihood table 12i. However, the disclosure is not necessarily limited thereto and may be configured such that the logarithmic likelihood $\log(L\_n)$ or the logarithmic likelihood $\log(L)$ calculated by Equation (3) or (4) is stored in the likelihood table 12i and the pattern selection in the process of step S34 of FIG. 11 and the tempo update in the processes of S35 to S37 are performed on the basis of the logarithmic likelihood $\log(L\_n)$ or the logarithmic likelihood $\log(L)$ stored in the likelihood table 12i.

The above embodiment is configured such that estimation of a state Jn and a pattern and switching of the output pattern to the estimated pattern are performed every time performance information of a key 2a is input. However, the disclosure is not limited thereto and may be configured such that estimation of a state Jn and a pattern and switching of the output pattern to the estimated pattern are performed on the basis of performance information within a predetermined time (for example, 2 bars or 4 bars). Thereby, switching of the output pattern is performed every at least the predetermined time, situations in which the output pattern, that is, the accompanist or the effect, is frequently switched are prevented and thus it is possible to provide accompaniment sounds and effects without discomfort to performers and audiences.

The above embodiment is configured such that performance information is input through the keyboard 2. However, alternatively, the disclosure may be configured such that a keyboard of an external MIDI standard is connected to the synthesizer 1 and performance information is input through such a keyboard.

The above embodiment is configured such that an accompaniment sound and a musical sound are output through the sound source 13, the DSP 14, the DAC 16, the amplifier 17 and the speaker 18 provided in the synthesizer 1. However, alternatively, the disclosure may be configured such that a sound source device of the MIDI standard is connected to the synthesizer 1 and an accompaniment sound and a musical sound of the synthesizer 1 are output through the sound source device.

The above embodiment is configured such that the performer's evaluation of the accompaniment sound and effect is performed through the user evaluation buttons 3. However, alternatively, the disclosure may be configured such that a sensor for detecting biological information of the performer, for example, a brain wave sensor for detecting brain waves of the performer (an example of the brain wave detection part), a cerebral blood flow sensor for detecting the cerebral blood flow of the performer, or the like is connected to the synthesizer 1 and the performer's evaluation is performed by estimating the performer's impression on the accompaniment sound and effect on the basis of the biological information.

The disclosure may also be configured such that a motion sensor for detecting the movement of the performer (an example of the motion detection part) is connected to the synthesizer 1 and the performer's evaluation is performed in accordance with a specific body gesture or hand gesture of the performer or the like detected by the motion sensor. In addition, the disclosure may be configured such that a facial expression sensor for detecting a facial expression of the performer (an example of the facial expression detection part) is connected to the synthesizer 1 and the performer's evaluation is performed in accordance with a specific facial expression of the performer detected by the facial expression sensor, for example, a facial expression or changes in the facial expression indicating the performer's good or poor impression, such as a smile or a dissatisfied facial expression. Further, the disclosure may be configured such that a posture sensor for detecting the posture of the performer (an example of the posture detection part) is connected and the performer's evaluation is performed in accordance with a specific posture (forward tilt or rearward tilt) of the performer or changes in the posture detected by the posture sensor.

The disclosure may also be configured such that, instead of the motion sensor, the facial expression sensor or the posture sensor, a camera for acquiring an image of the performer is connected to the synthesizer 1 and the movement, expression or posture of the performer is detected by analyzing the image acquired by the camera to perform the performer's evaluation. By performing the performer's evaluation in accordance with detection results from the sensor for detecting biological information, the motion sensor, the expression sensor, the posture sensor, or the camera, the performer can evaluate the accompaniment sound or effect without operating the user evaluation buttons 3, and therefore it is possible to improve operability of the synthesizer 1.

The above embodiment is configured such that the user evaluation likelihood involves the performer's evaluation on the accompaniment sound or effect. However, the disclosure is not necessarily limited thereto and may be configured such that the user evaluation likelihood involves the audience's evaluation on the accompaniment sound or effect or involves evaluations of the performer and the audience on the accompaniment sound or effect. In such a case, the disclosure may be configured such that remote control devices for transmitting the audience's high or low evaluation on the accompaniment sound or effect to the synthesizer 1 are given to the audience and the user evaluation likelihood is calculated on the basis of evaluation numbers of high and low evaluations from the remote control devices. Further, the disclosure may be configured such that a microphone is disposed on the synthesizer 1 and the user evaluation likelihood is calculated on the basis of the magnitude of cheers from the audience.

The above embodiment is configured such that the control program 11a is stored in the flash ROM 11 of the synthesizer 1 and operates on the synthesizer 1. However, the disclosure is not limited thereto and may be configured such that the control program 11a is caused to operate on another computer such as a personal computer (PC), a mobile phone, a smartphone, or a tablet terminal. In this case, the disclosure may be configured such that performance information is input through a keyboard of the MIDI standard or a character input keyboard connected to the PC or the like by wire or wirelessly, instead of through the keyboard 2 of the synthesizer 1, or may be configured such that performance information is input through a software keyboard displayed on a display device of a PC or the like.

The numerical values stated in the above embodiments are merely examples and other numerical values can of course be adopted.

It will be apparent to those skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:

1. An automatic performance device comprising:
   a storage part configured to store a plurality of performance patterns;
   a performance part configured to play a performance on the basis of one of the plurality of performance patterns stored in the storage part;
   an input part configured to input performance information through an input device configured to receive a performance operation of a user;
   a selection part configured to select a performance pattern being a maximum likelihood estimation from the plurality of performance patterns stored in the storage part on the basis of the performance information input to the input part; and
   a switching part configured to switch some or more musical expressions of the performance pattern that is being played by the performance part to a musical expression of the performance pattern selected by the selection part.

2. The automatic performance device according to claim 1, further comprising a likelihood calculation part configured to calculate a first likelihood for each of all or some of musical sounds included in the plurality of performance patterns stored in the storage part on the basis of the performance information input to the input part,
wherein the selection part is configured to estimate one of the plurality of performance patterns stored in the storage part to be the maximum likelihood estimation on the basis of the first likelihood calculated by the likelihood calculation part.

3. The automatic performance device according to claim 2, wherein the likelihood calculation part is configured to calculate the first likelihood for each of all or some of the musical sounds included in the plurality of performance patterns stored in the storage part on the basis of a pitch of the performance information input to the input part.

4. The automatic performance device according to claim 2, wherein the likelihood calculation part is configured to calculate the first likelihood for each of all or some of the musical sounds included in the plurality of performance patterns stored in the storage part on the basis of a beat position of the performance information input to the input part.

5. The automatic performance device according to claim 2, wherein the likelihood calculation part is configured to calculate the first likelihood that a musical sound is generated subsequent to another musical sound for each of all or some of the musical sounds included in the plurality of performance patterns stored in the storage part on the basis of an input interval between previous performance information and current performance information that have been input to the input part.

6. The automatic performance device according to claim 2, further comprising an evaluation input part configured to input an evaluation of the user.

7. The automatic performance device according to claim 6, further comprising a likelihood reflection part configured to reflect the input evaluation in a second likelihood of the musical expression of the performance pattern that is being played by the performance part, when the evaluation has been input to the evaluation input part.

8. The automatic performance device according to claim 7, wherein the likelihood calculation part is configured to calculate the first likelihood for each of all or some of the musical sounds included in the plurality of performance patterns stored in the storage part on the basis of the second likelihood reflected by the likelihood reflection part.

9. The automatic performance device according to claim 6, wherein the evaluation input part includes a brain wave detection part configured to detect a brain wave of the user and a receiving part configured to receive an output of the brain wave detection part after converting the output of the brain wave detection part into the evaluation of the user.

10. The automatic performance device according to claim 6, wherein the evaluation input part includes a motion detection part configured to detect movement of the user and a receiving part configured to receive a detection result of the motion detection part after converting the detection result into the evaluation of the user.

11. The automatic performance device according to claim 6, wherein the evaluation input part includes a facial expression detection part configured to detect a facial expression of the user and a receiving part configured to receive an output of the facial expression detection part after converting the output of the facial expression detection part into the evaluation of the user.

12. The automatic performance device according to claim 6, wherein the evaluation input part includes a posture detection part configured to detect a posture of the user and a receiving part configured to receive an output of the posture detection part after converting the output of the posture detection part into the evaluation of the user.

13. The automatic performance device according to claim 1, wherein the switching part is configured to switch at least one of a pattern, a chord progression, an arpeggio setting, an effect setting, a volume or velocity value, and a timbre parameter value, which constitute the performance pattern among musical expressions of the performance pattern that is being played by the performance part to the musical expression of the performance pattern selected by the selection part.

14. An automatic performance device comprising:
a storage part configured to store a plurality of performance patterns;
a performance part configured to play a performance on the basis of one of the plurality of performance patterns stored in the storage part;
an input part configured to input performance information through an input device configured to receive a performance operation of a user; and
a selection part configured to select a performance pattern being a maximum likelihood estimation from the plurality of performance patterns stored in the storage part on the basis of the performance information input to the input part,
wherein the selection part is configured to execute a selection process of the performance pattern when performance information based on the performance operation of the user has been input to the input part.

15. An automatic performance device comprising:
a storage part configured to store a plurality of performance patterns;
a performance part configured to play a performance on the basis of one of the plurality of performance patterns stored in the storage part;
an input part configured to input performance information through an input device configured to receive a performance operation of a user;
a selection part configured to select a performance pattern being a maximum likelihood estimation from the plurality of performance patterns stored in the storage part on the basis of the performance information input to the input part; and
an ending portion configured to shift the performance pattern that is being played by the performance part to an ending part of the performance pattern when performance information based on the performance operation of the user has not been input to the input part for a predetermined period of time or longer.

16. An automatic performance method causing a computer to execute automatic performance, the automatic performance method causing the computer to:
store a plurality of performance patterns;
play a performance on the basis of one of the stored plurality of performance patterns;
input a performance operation of a user as a performance information;
select a performance pattern being a maximum likelihood estimation among the plurality of stored performance patterns on the basis of the input performance information and execute automatic performance with the selected performance pattern; and switch some or more musical expressions of the performance pattern that is being played to a musical expression of the selected performance pattern.

17. The automatic performance method according to claim 16, wherein a first likelihood is calculated for each of all or some of musical sounds included in the plurality of stored performance patterns on the basis of the input performance information, and
one of the plurality of stored performance patterns is the maximum likelihood estimation on the basis of the calculated first likelihood.

18. The automatic performance method according to claim 17, wherein an evaluation of the user is input,
when the evaluation has been input, the input evaluation is reflected in a second likelihood of the musical expression of the performance pattern that is being played, and
the first likelihood is calculated for each of all or some of the musical sounds included in the plurality of stored performance patterns on the basis of the reflected second likelihood.

19. An automatic performance method causing a computer to execute automatic performance, the automatic performance method causing the computer to:

store a plurality of performance patterns;

play a performance on the basis of one of the stored plurality of performance patterns;

input a performance operation of a user as a performance information;

select a performance pattern being a maximum likelihood estimation among the plurality of stored performance patterns on the basis of the input performance information and execute automatic performance with the selected performance pattern; and execute a selection process of the performance pattern when performance information based on the performance operation of the user has been input.

* * * * *